Figure 1:
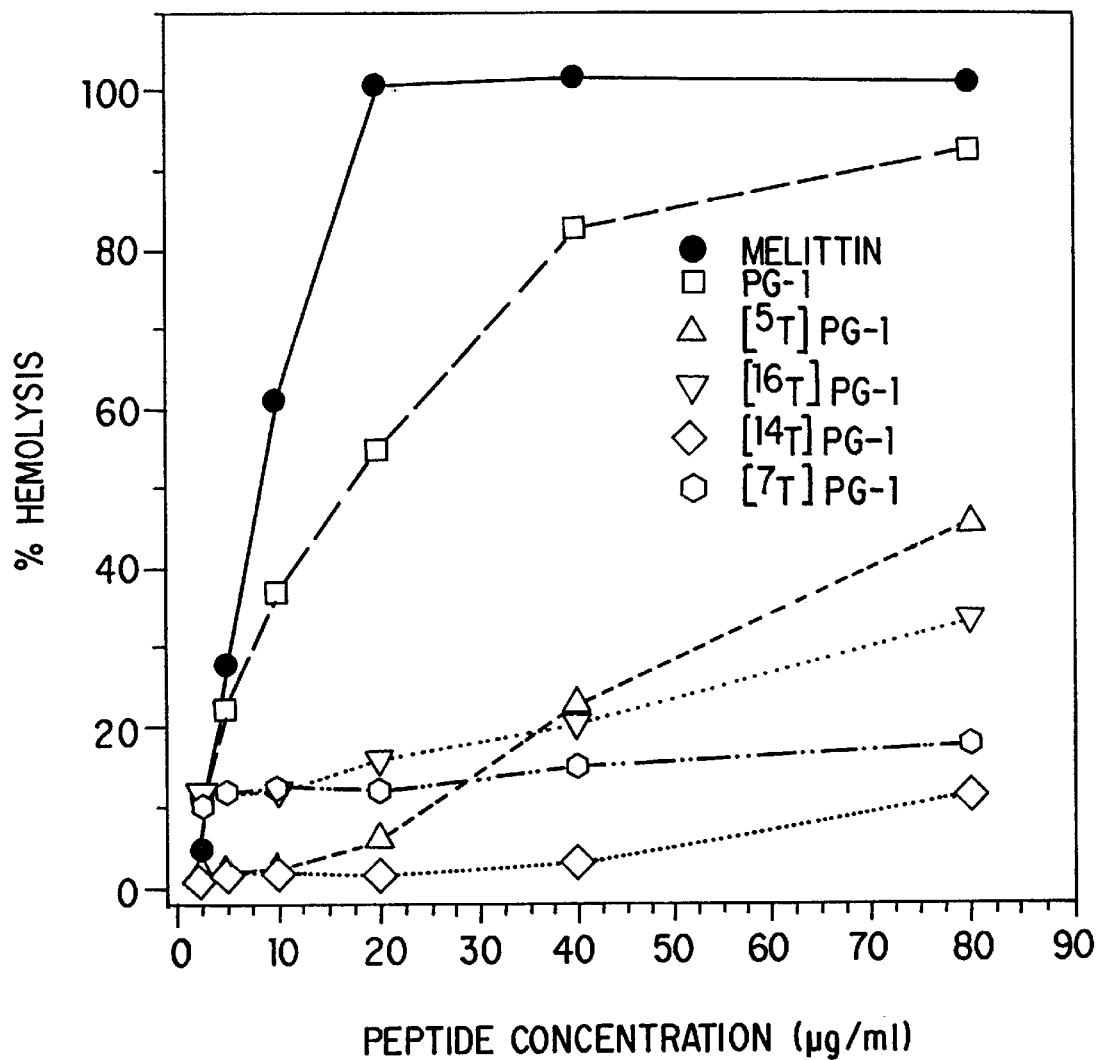

United States Patent [19]
Chang et al.

[11] Patent Number: 6,043,220
[45] Date of Patent: *Mar. 28, 2000

[54] THREONINE-CONTAINING PROTEGRINS

[75] Inventors: Conway C. Chang, San Francisco; Jie Chen, Belmont; Robert I. Lehrer, Santa Monica; Peggy A. Radel, Berkeley, all of Calif.

[73] Assignee: IntraBiotics Pharmaceuticals, Inc., Mountain View, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/984,294

[22] Filed: Dec. 3, 1997

[51] Int. Cl.$^7$ .......................... A61K 38/08; A61K 38/10; A61K 38/16; C07K 7/08

[52] U.S. Cl. ............................... 514/12; 514/13; 514/14; 514/15; 530/324; 530/325; 530/326; 530/327; 530/328

[58] Field of Search ...................... 530/324, 325, 530/326, 327, 328; 514/12, 13, 14, 15

[56] References Cited

U.S. PATENT DOCUMENTS

| | | | |
|---|---|---|---|
| 5,434,074 | 7/1995 | Gibson et al. | 435/219 |
| 5,464,823 | 11/1995 | Lehrer et al. | 514/13 |
| 5,693,486 | 12/1997 | Lehrer et al. | 435/69.1 |
| 5,708,154 | 1/1998 | Smith et al. | 536/23.1 |
| 5,804,558 | 9/1998 | Lehrer et al. | 514/13 |
| 5,994,306 | 11/1999 | Chang et al. | 514/13 |

FOREIGN PATENT DOCUMENTS

| | | |
|---|---|---|
| 0 545 730 | 6/1993 | European Pat. Off. . |
| WO 95/03325 | 2/1995 | WIPO . |
| WO 96/04373 | 2/1996 | WIPO . |
| WO 96/37508 | 11/1996 | WIPO . |
| WO 97/02287 | 1/1997 | WIPO . |
| WO 97/18826 | 5/1997 | WIPO . |
| WO 97/18827 | 5/1997 | WIPO . |
| WO 98/03192 | 1/1998 | WIPO . |

OTHER PUBLICATIONS

Dayhoff. Atlas of Protein Sequencing and Structure. vol. 5, p. 96, 1972.

Schulz et al. Principles of Protein Structure, New York, Springer–Verlag, pp. 14–16, 1979.

Harwig et al., 1995, "Determination of Disulphide Bridges in PG–2, an Anti–microbial Peptide from Porcine Leukocytes", *Journal of Peptide Science*, 3:207–215.

Hu et al., 1991, "Isolation and Characterization of Corticostatic Peptides from Guinea Pig Bone Marrow," *Biochem. Biophys. Res. Commun.* 180:558–565.

Kokryakov et al., 1993, "Protegrins: leukocyte antimicrobial peptides that combine features of corticostatic defensins and tachyplesins", *FEBS Letters* 327(2):231–236.

Masuda et al., 1992, "A novel anti–HIV synthetic peptide, T–22 ([Tyr5,12,Lys7]–polyphemusin II)," *Biochem. Biophys. Res. Commun.* 189(2):845–850.

Matsuzaki et al., 1991, "Interactions of an antimicrobial peptide, tachyplesin I, with lipid membranes", *Biochimica et Biophysica Acta.*, 1070:259–264.

Matsuzaki et al., 1993, "Role of Disulfide Linkages in Tachyplesin–Lipid Interactions", *Biochemistry*, 32(43):11704–11710.

Mirgorodskaya et al., 1993, "Primary Structure of three cationic peptides from porcine neutrophils", *FEBS*, 330(3):339–342.

Muta et al., 1990, "Tachyplesins isolated from hemocytes of Southeast Asian horseshoe crabs (*Carcinoscorpius rotundicauda* and *Tachypleus gigas*): identification of a new tachyplesin, tachyplesin III, and a processing intermediate of its precursor," *J. Biochem (Tokyo)* 108(2):261–266.

(List continued on next page.)

*Primary Examiner*—Jeffrey E. Russel
*Attorney, Agent, or Firm*—Pennie & Edmonds LLP

[57] ABSTRACT

The invention is directed to antimicrobial peptides related to naturally-occurring protegrin peptides, and methods of using the peptides in a variety of contexts, including the treatment or prevention of infections, and diseases related thereto.

29 Claims, 6 Drawing Sheets

OTHER PUBLICATIONS

Otaka et al., 1994, "Molecular parameters for the anti–human immunodeficiency virus activity of T22 ([Tyr5,12, Lys7]–polyphemusin II)," *Biol. Pharm. Bull.* 17(12):1669–1672.

Park et al., 1992, "Conformation of Tachyplesin I from *Tachypleus tridentatus* When Interacting with Lipid Matrices", Biochemistry, 31(48):12241–12247.

Sonis, Ch. XL–14 "Oral Complications", *Complications of Cancer and Their Treatments,* pp. 2381–2388 (Not Dated).

Sonis, Section 6 "Oral Complications of Cancer Therapy", *Adverse Effects of Treatment–Oral Complications of Cancer Chemotherapy,* pp. 2385–2394 (Not Dated).

Soto et al., 1995, "Mapping of the linear antigenic determinants from the *Leishmania infantum* histone H2A recgonized by sera from dogs with leishmaniasis", *Immunology Letters,* 4:209–214.

Storici and Zanetti, 1993, "A Novel cDNA Sequence Encoding a Pig Leukocyte Antimicrobial Peptide with a Cathelin–Like Pro–Sequence", *Biochemical and Biophysical Research Communications,* 196(3):1363–1368.

Tamamura et al., 1993, "Antimicrobial Activity and Conformation of Tachyplesin I and its Analogs", *Chemical and Pharmaceutical Bulletin,* 41(5):978–980.

Tamamura et al., 1993, "A comparative study of the solution structures of tachyplesin I and a novel anti–HIV synthetic peptide T22 ([$Tyr^{5,12}$,$Lys^7$]–polyphemusin II), determined by nuclear magnetic resonance", *Biochimica et Biophysica Acta.,* 1163:209–216.

Zhao et al., 1994, "Identification of a new member of the protegrin family by cDNA cloning", *FEBS Letters,* 346:285–288.

Zhao et al., 1995, "The structure of porcine protegrin genes", *FEBS Letters,* 368:197–202.

Zhao et al., 1995, "Structures of genes for two cathelin–associated antimicrobial peptides: prophenin–2 and PR–39", *FEBS Letters,* 376:130–134.

THREONINE-CONTAINING PROTEGRINS

1. FIELD OF THE INVENTION

The invention relates to the field of antimicrobial peptides. In particular, the invention concerns short peptides designated "protegrins," that have a wide range of antimicrobial activities.

2. BACKGROUND OF THE INVENTION

With the recent dramatic rise of antibiotic-resistant pathogens and infectious diseases, the need for new antimicrobial agents is urgent (Cohen et al., 1992, *Science* 257:1050–1055). For example, strains of *Enterococcus faecium* that are resistant to vancomycin have recently been observed (Moellering, 1990, *Clin. Microbiol. Rev.* 3:46–65). As vancomycin is considered to be the antibiotic of last resort for several pathogens, strains resistant to vancomycin pose a serious health threat to society. Despite this urgency, in more than ten years only one completely different type of antibiotic, a streptogramin mixture called Synercid (Rhone-Poulenc Rorer, Collegeville, Pa.), has reached Phase III clinical trials (Pfeiffer, 1996, "New Anti-Microbial Therapies Described," *Genetic Engineering News* 16(8):1).

Recently, a new class of antimicrobial or antibiotic agents based on naturally-occurring antimicrobial peptides produced within plants, animals and insects have been discovered. These peptides include, among others, cecropins (Hultmark et al., 1980, *Eur. J. Biochem.* 106:7–16; Hultmark et al., 1982, *Eur. J. Biochem.* 127:207–217), apidaecins (Casteels et al., 1989, *EMBO J.* 8:2387–2391), magainins (Zasloff, 1987, *Proc. Natl. Acad. Sci. U.S.A.* 84:5449–5453; Zasloff et al., 1988, *Proc. Natl. Acad. Sci. U.S.A.* 85:910–913), tachyplesins and analogues of tachyplesins such as polyphemusins (Nakamura et al., 1988, *J. Biol. Chem.* 263:16709–16713; Miyata et al., 1989, *J. Biochem.* 106:663–668), defensins (Lehrer et al., 1991, *Cell* 64:229–230; Lehrer et al., 1993, *Ann. Rev. Immunol.* 11:105–128; U.S. Pat. No. 4,705,777; U.S. Pat. No. 4,659,692; U.S. Pat. No. 4,543,252), β-defensins (Selsted et al., 1993, *J. Biol. Chem.* 288:6641–6648; Diamond et al., 1991, *Proc. Natl. Acad. Sci. U.S.A.* 88:3952–3958), insect defensins (Lambert et al., 1989, *Proc. Natl. Acad. Sci. U.S.A.* 88:262–265; Matsuyama and Natori, 1988, *J. Biol. Chem.* 263:17112–17116), and protegrins (Kokryakov et al., 1993, *FEBS* 337:231–236; Zhao et al., 1994, *FEBS Letters* 346:285–288; Migorodskaya et al., 1993, *FEBS* 330:339–342; Storici et al., 1993, *Biochem. Biophys. Res. Commun.* 196:1363–1367; Zhao et al., 1994, *FEBS Lett.* 346:285–288; Manzoni et al., 1996, *FEBS Lett.* 383:93–98; U.S. Pat. No. 5,464,823). The discovery of these new classes of antimicrobial peptides offers hope that some might be developed into agents that can be used against microorganisms of medicinal importance. Those of animal origin are of particular importance, as these antimicrobial peptides generally exhibit activity against antibiotic-resistant bacterial strains and have a lower frequency of resistance as compared to conventional antibiotics (Steinberg et al., 1996, "Protegrins: Fast Acting Bactericidal Peptides," *presented at: Intl. Symposium on Staphylococci and Staphylococcus Infections*, Aix les Bains, France). At least one of these peptides, called Cytolex™ (Magainin Pharmaceuticals, Inc.), is currently in Phase III clinical trials for infections associated with diabetic foot ulcers (Craig, Aug. 17, 1995, *BioWorld Today* 6(158):1).

One particularly interesting class of antimicrobial peptides are those which have been isolated from porcine leukocytes, designated "protegrins". In addition to the five naturally-occurring protegrins, designated PG-1, PG-2, PG-3, PG-4 and PG-5, respectively, several active congeners have been described (see, e.g., U.S. Pat. No. 5,464,823; WO 95/03325; WO 96/37508). The protegrin peptides, which are generally amphiphilic in nature, exhibit antimicrobial activity against a broad spectrum of microbes, including viruses, retroviruses, bacteria, fungi, yeast and protozoa. In addition, they bind to endotoxins, i.e., the lipopolysaccharide (LPS) compositions derived from Gram-negative bacteria that are believed to be responsible for Gram-negative sepsis. Thus, these peptides are useful as antibacterial, anti-fungal and antiviral agents in both plants and animals. For a review of the literature concerning protegrin peptides, see, Kokryakov et al., 1993, *FEBS Lett* 337:231–236; Zhao et al., 1994, *FEBS Lett* 346:285–288; Mirgorodskaya et al., 1993, *FEBS Lett* 330:339–342; Storici et al., 1993, *Biochem Biophys Res Comm* 196:1363–1367; Harwig et al., 1995, *J Peptide Sci* 3:207; Zhao et al., 1995, *FEBS Lett* 376:130–134; Zhao et al., 1995, *FEBS Lett* 368:197–202; Miyakawa et al., 1996, *Infect Immun* 64:926–932; Yasin et al., 1996, *Infect Immun* 64:709–713; Qu et al., 1996, *Infect Immun* 64:1240–1245; Aumelas et al., 1996, *Eur J. Biochem* 237:575–583; Mangoni et al., 1996, *FEBS Lett* 383:93–98; Steinberg et al., 1996, "Protegrins: Fast Acting Bacterial Peptides," presented at 8*th Intl. Symposium on Staphylococci and Staphylococcal Infections*, Aix les Bains, France, Jun. 23–26, 1996; Steinberg et al., 1996, "Broad Spectrum Antimicrobial Activity of Protegrin Peptides," presented at 36*th Interscience Conference on Antimicrobial Agents and Chemotherapy*, New Orleans, La., Sep. 15–18, 1996; Kung et al., 1996, "Protegrin Protects Mice From Systemic Infection By Antibiotic-Resistant Pathogens," presented at 36*th Interscience Conference on Antimicrobial Agents and Chemotherapy*, New Orleans, La., Sep. 15–18, 1996; and Steinberg et al., 1996, "In Vitro Efficacy of Protegrins Against *Helicobacter pylori*," presented at 36*th Interscience Conference on Antimicrobial Agents and Chemotherapy*, New Orleans, La., Sep. 15–18, 1996.

In use, protegrin peptides provide myriad advantages over conventional antibiotics and other antimicrobial peptides. For example, unlike defensin peptides, protegrin peptides effect their broad spectrum activity under physiological conditions, including in the presence of physiological saline. Due to their small size, they can be prepared in non-immunogenic form, extending the number of species to which they can be administered. Moreover, since the protegrin peptides are related to antimicrobial peptides found naturally in animals, they do not exhibit the high frequency of resistance observed with traditional antibiotics. Thus, the protegrin peptides are particularly useful for treating or preventing infections caused by antibiotic-resistant pathogens.

The present invention is directed to a new set of protegrin peptides which offer improved serum compatibility, and hence improved utility as systemic antibiotics, as well as decreased hemolytic activity against human red blood cells as compared with the naturally-occurring protegrins, while at the same time providing broad spectrum activity with a low frequency of resistance.

3. SUMMARY OF THE INVENTION

In one aspect, the present invention is directed to protegrin peptides having improved serum compatibility and reduced hemolytic activity against human red blood cells than the naturally-occurring protegrins. The protegrins of the invention are generally composed of about 10–30 amino acid residues and are characterized by a "core" structure having two main elements: a reverse-turn bracketed by two strands that form an anti-parallel β-sheet. The β-sheet region of the molecule is amphiphilic, one surface being net hydrophobic in character, the other being net hydrophilic in character. The peptides contain at least one basic amino acid residue in the reverse-turn region, and have a net charge of at least +1 at physiological pH. The peptides are further characterized by having amino acids with hydroxyl side chains, such as threonine or serine, at certain invariant positions within the core structure. The protegrin peptides may optionally be acylated at the N-terminus and/or amidated or esterified at the C-terminus, and may contain zero, one or two disulfide bridges.

In one illustrative embodiment, the invention provides protegrin peptides composed of about 10–30 amino acid residues and comprising the amino acid sequence:

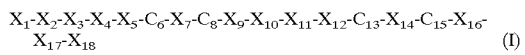

$$X_1\text{-}X_2\text{-}X_3\text{-}X_4\text{-}X_5\text{-}C_6\text{-}X_7\text{-}C_8\text{-}X_9\text{-}X_{10}\text{-}X_{11}\text{-}X_{12}\text{-}C_{13}\text{-}X_{14}\text{-}C_{15}\text{-}X_{16}\text{-}X_{17}\text{-}X_{18} \quad (I)$$

or a pharmaceutically acceptable salt or N-terminal acylated or C-terminal amidated or esterified form thereof, wherein:

each of $C_8$ and $C_{13}$ is independently present or not present, and if present each is independently a cysteine-like, basic, small, polar or hydrophobic amino acid;

each of $C_6$ and $C_{15}$ is independently a cysteine-like, basic, small, polar or hydrophobic amino acid;

each of $X_1$, $X_2$, $X_3$, $X_4$ and $X_5$ is independently present or not present, and if present each is independently a basic, hydrophobic, polar or small amino acid;

each of $X_7$ and $X_{14}$ is independently a hydrophobic or a small amino acid;

each of $X_9$ and $X_{12}$ is independently present or not present;

$X_9$–$X_{12}$ taken together are capable of effecting a reverse-turn when contained in the amino acid sequence of formula (I) and at least one of $X_9$–$X_{12}$ must be a basic amino acid;

each of $X_{16}$, $X_{17}$ and $X_{18}$ is independently present or not present, and if present each is independently a basic, hydrophobic, polar or small amino acid; and at least about 15% up to about 50% of the amino acids comprising the antimicrobial peptide are basic amino acids such that the antimicrobial peptide has a net charge of at least +1 at physiological pH, with the proviso that at least one of $X_2$, $X_3$, $X_5$, $X_7$, $X_{14}$ or $X_{16}$ must be a small amino acid, preferably a hydroxyl-containing amino acid.

The peptides of the invention exhibit broad spectrum antimicrobial activity, being biocidal against a wide range of microbial targets, including Gram-positive bacteria, Gram-negative, bacteria, yeast, fungi and protozoa. Accordingly, the peptides can be used as antimicrobial agents in a wide variety of applications. For example, the peptides can be used to preserve or disinfect a variety of materials, including medical equipment, foodstuffs, cosmetics, contact lens solutions, medicaments or other nutrient-containing materials. The peptides are also useful for the prophylaxis or treatment of microbial infections or diseases related thereto in both plants and animals.

In another aspect, the invention is directed to recombinant materials useful for the production of certain of the peptides of the invention as well as plants or animals modified to contain expression systems for the production of these peptides.

In another aspect, the invention is directed to pharmaceutical compositions and to compositions for application to plants containing the peptides of the invention as active ingredients or compositions which contain expression systems for production of the peptides or for in situ expression of the nucleotide sequence encoding these peptides.

In yet another aspect, the present invention is directed to methods of using the above-described peptides, or compositions thereof, to inhibit microbial growth. The method generally involves contacting a microbe with an amount of one or more of the protegrin peptides or compositions of the invention effective to inhibit the growth of the microbe. In a preferred embodiment, the microbe is a bacteria.

In a final aspect, the present invention is directed to methods of using the above-described peptides, or compositions thereof, to prevent or treat microbial infections or diseases related thereto in both plants and animals, including humans. The method generally involves administering to a plant or animal an amount of one or more of the peptides or compositions of the invention effective to treat or prevent the particular indication. Diseases or infections which can be treated or presented with the protegrin peptides of the invention include eye infections such as conjunctivitis and keratitis, corneal ulcers, stomach ulcers associated with *H. pylori*, sexually transmitted diseases (STDs), and Gram-negative sepsis. Clinically relevant infections that can be treated or prevented by the protegrin peptides of the invention include systemic infections caused by multi-drug resistant pathogens such as vancomycin-resistant *Enterococcus faecium*, methicillin-resistant *Staphylococcus aureus* and penicillin-resistant *Streptococcus pneumoniae*.

4. BRIEF DESCRIPTION OF THE DRAWINGS

Figure 2:
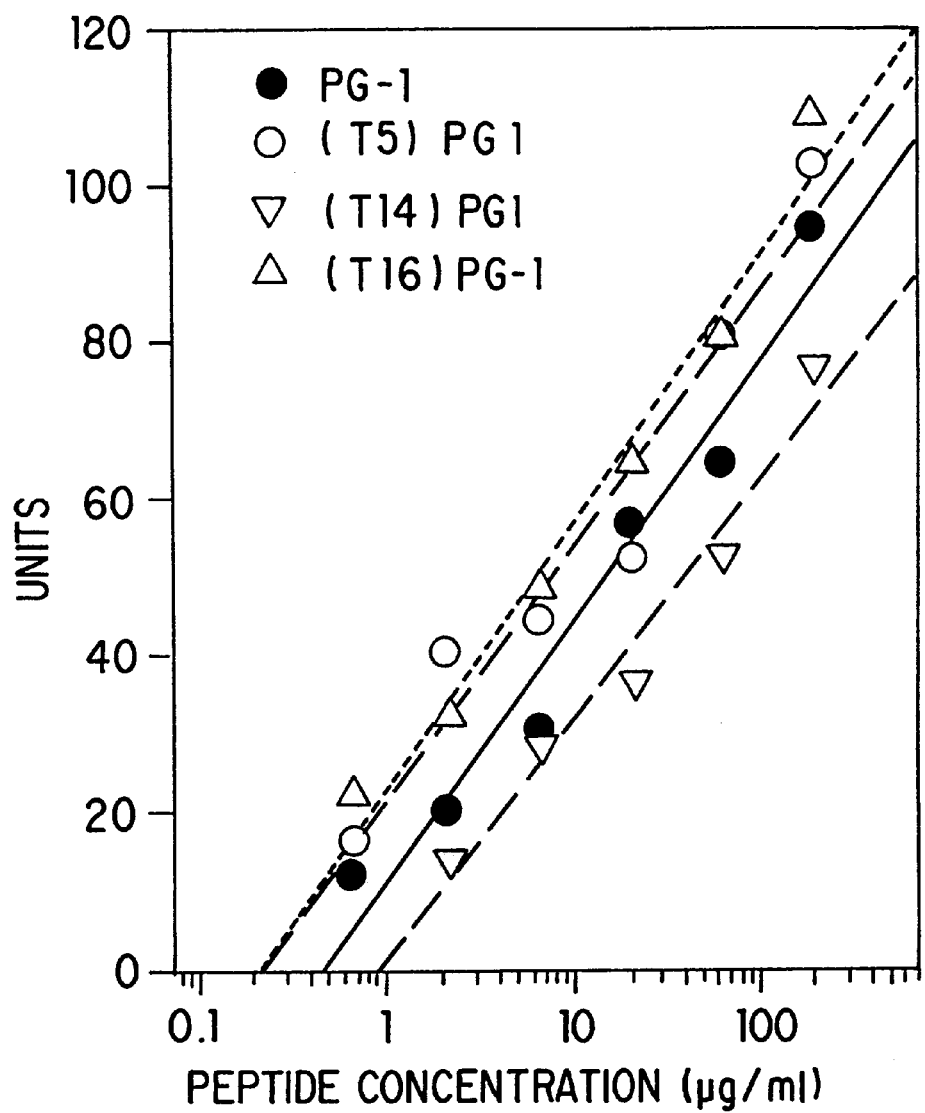
Figure 3:
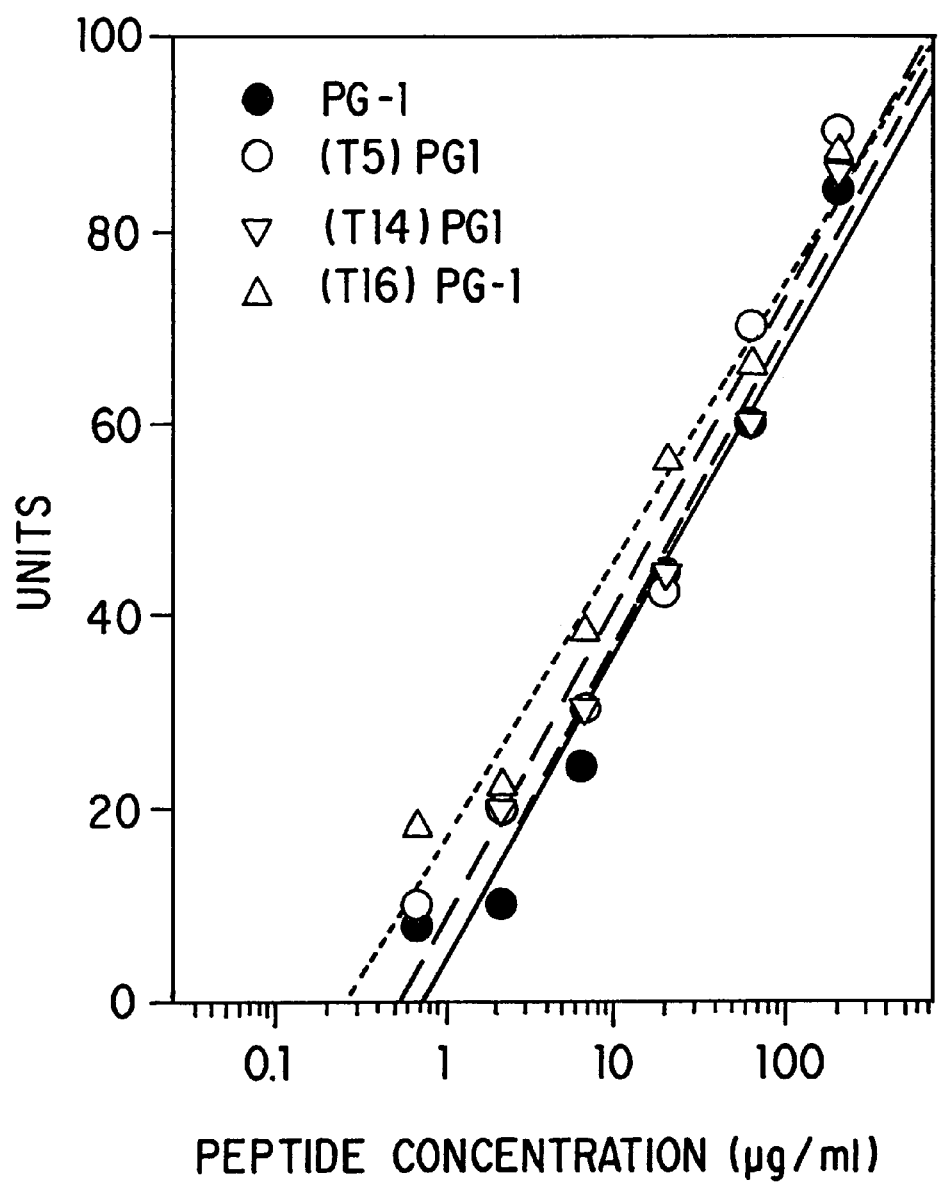
Figure 4:
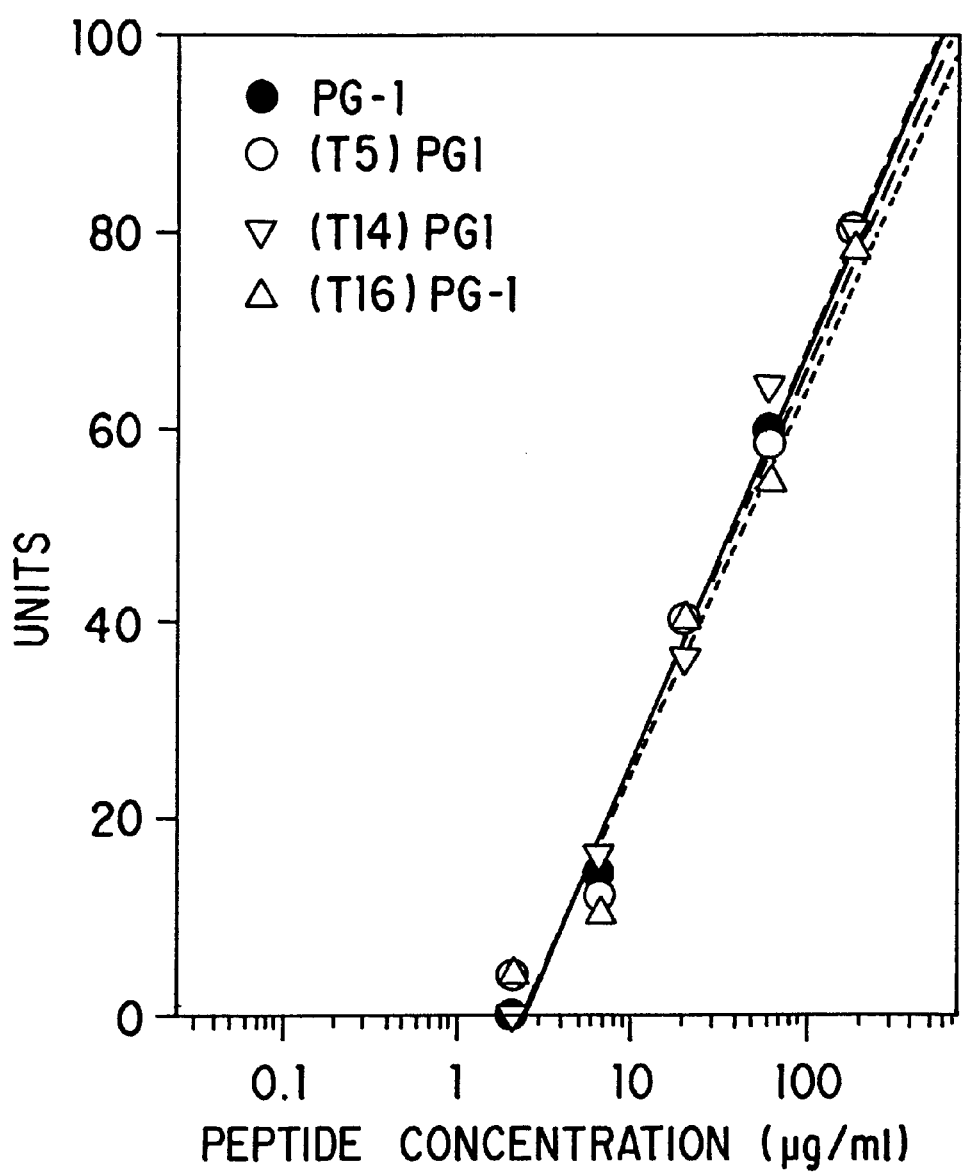
Figure 5:
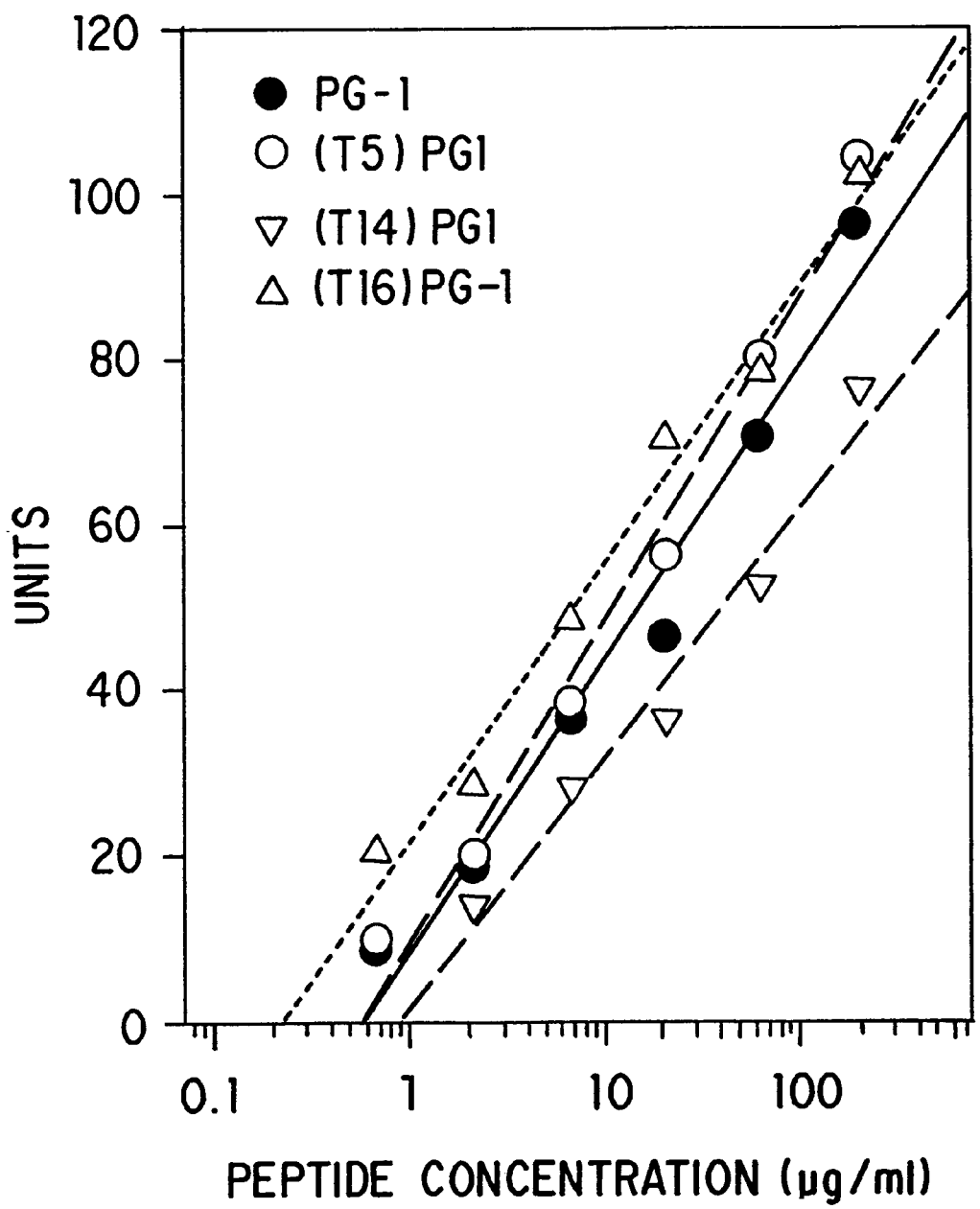
Figure 6:
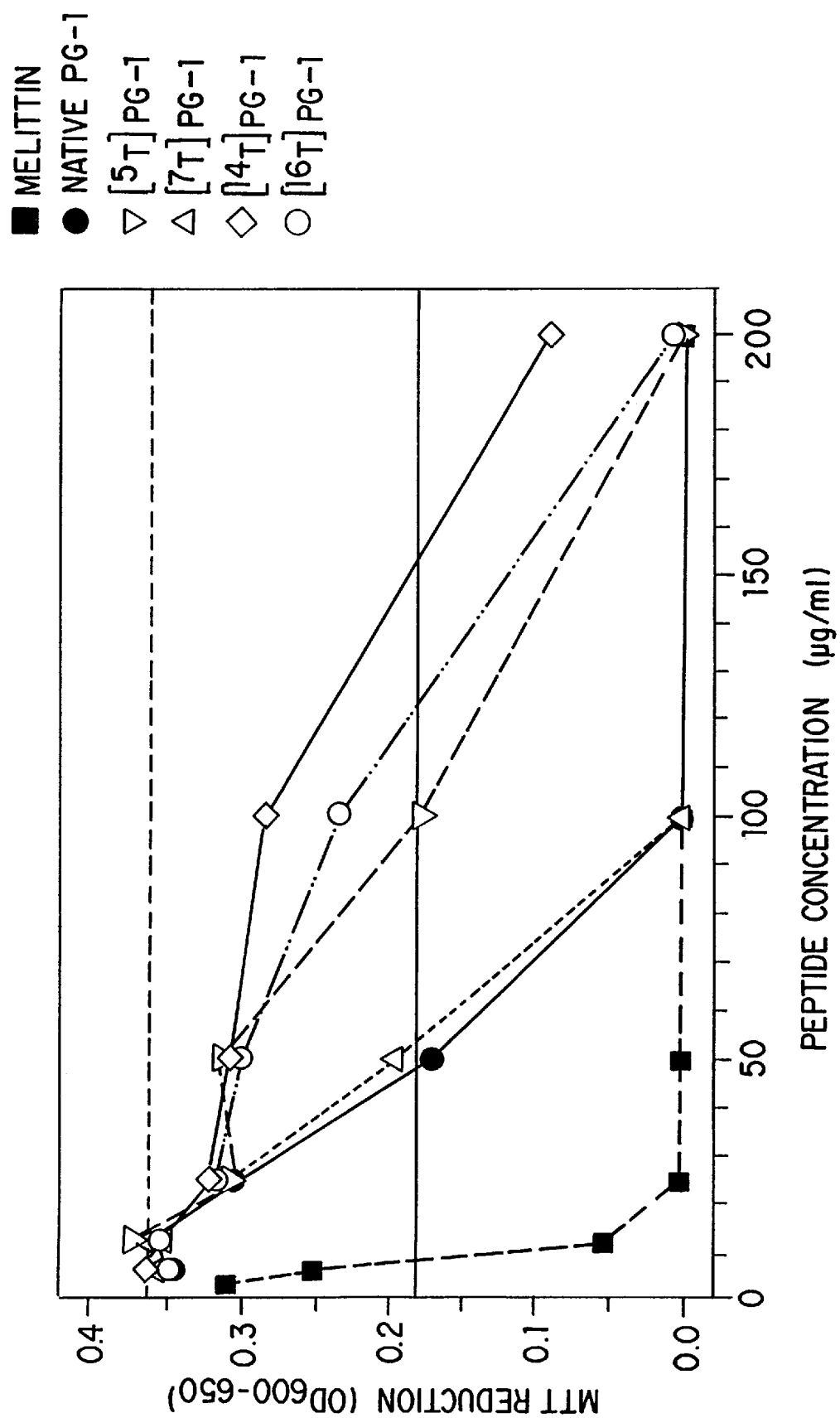

FIG. 1 provides a graph illustrating the decreased hemolytic activity of [$^5$T]PG-1 (RGGRTCYCRRRFCVCVGR-NH$_2$; SEQ ID NO:3; Δ), [$^7$T]PG-1 (RGGRLCTCRRRFCVCVGR-NH$_2$; SEQ ID NO:5;○), [$^{14}$T]PG-1 (RGGRLCYCRRRFCTCVGR-NH$_2$); SEQ ID NO:6;◇) and 16[$^6$T]PG-1 (RGGRLCYCRRRFCVCTGR-NH$_2$; SEQ ID NO:8; ▽) against human red blood cells as compared with native PG-1 (RGGRLCYCRRRFCVCVGR-NH$_2$; SEQ ID NO:1; □) and melittin (SEQ ID NO:19; ●);

FIG. 2 provides a graph illustrating the antimicrobial activity of [$^5$T]PG-1 (SEQ ID NO:3; ○), [$^{14}$T]PG-1(SEQ ID NO:6; ▽) and [$^{16}$T]PG-1 (SEQ ID NO:8; Δ) against *E. coli* ML-35 as compared with native PG-1 (SEQ ID NO:1; ●);

FIG. 3 provides a graph illustrating the antimicrobial activity of [$^5$T]PG-1 (SEQ ID NO:3; ○), [$^{14}$T]PG-1 (SEQ ID NO:6; ▽) and [$^{16}$T]PG-1 (SEQ ID NO:8; Δ) against *P. aeruginosa* as compared with native PG-1 (SEQ ID NO:1●);

FIG. 4 provides a graph illustrating the antimicrobial activity of [$^5$T]PG-1 (SEQ ID NO:3; ○), [$^{14}$T]PG-1 (SEQ ID NO:6; ▽) and [$^{16}$T]PG-1 (SEQ ID NO:8; Δ) against *C. ablicans* as compared with native PG-1 (SEQ ID NO:1; ●);

FIG. 5 provides a graph illustrating the antimicrobial activity of [$^5$T]PG-1 (SEQ ID NO:3; ○), [$^{14}$T]PG-1 (SEQ ID NO:6; ▽) and [$^{16}$T]PG-1 (SEQ ID NO:8; Δ) against *L. monocytogenes* as compared with native PG-1 (SEQ ID NO:1; ●); and FIG. 6 provides a graph illustrating the cytotoxicity of [$^5$T]PG-1 (SEQ ID NO:3; ○), [$^7$T]PG-1 (SEQ ID NO:5; Δ) [$^{14}$T]PG-1 (SEQ ID NO:6; ◇) and [$^{16}$T]PG-1 (SEQ ID NO:8; Δ) against ME-180 cells as compared with native PG-1 (SEQ ID NO:1; ●) and melittin (SEQ ID NO:19; ■), as measured by the MTT assay.

5. DETAILED DESCRIPTION OF THE INVENTION

5.1 Definitions

As used herein, the following terms shall have the following meanings:

"Secondary Structure:" As used herein, "secondary structure" refers to the regular local structure of segments of polypeptide chains including, but not limited to, helices such as α-helices, extended strands such as β-strands and sheets of extended strands such as β-sheets.

"Anti-Parallel β-Sheet:" As used herein "anti-parallel β-sheet" refers to a secondary structure of a polypeptide chain characterized by intermolecular backbone-backbone hydrogen bonding between anti-parallel peptide strands. An anti-parallel β-sheet may optionally contain one or two interstrand disulfide linkages.

"Amphiphilic Anti-Parallel β-Sheet:" As used herein, "amphiphilic anti-parallel β-sheet" refers to an anti-parallel β-sheet wherein one surface has a net hydrophobic character and another surface has a net hydrophilic character.

"Reverse-Turn:" As used herein, "reverse-turn" refers to a characteristic secondary structure that links adjacent strands of an anti-parallel β-sheet. Typically, a "reverse-turn" is a two to four amino acid residue peptide segment that reverses the direction of a polypeptide chain so as to allow a single polypeptide chain to adopt an anti-parallel β-sheet conformation. Such peptide segments are well known in the art and include, by way of example and not limitation, three amino acid residue γ-turns (Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394) and four amino acid residue β-turns, as described below.

"βTurn:" As used herein, "β-turn" refers to a recognized sub-class of reverse-turns. Typically, a "β-turn" is a four amino acid residue peptide segment that reverses the direction of a polypeptide chain so as to allow a single polypeptide chain to adopt an anti-parallel β-sheet secondary structure. Generally, the two internal amino acid residues of the β-turn are not involved in the hydrogen-bonding of the β-sheet; the two amino acid residues on either side of the internal residues are included in the hydrogen-bonding of the β-sheet. The term "β-turn" expressly includes all types of peptide β-turns commonly known in the art including, but not limited to, type-I, type-II, type-III, type-I', type-II' and type-III' β-turns (see, Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394).

"Antimicrobially Effective Amount:" As used herein, "antimicrobially effective amount" refers to an amount of peptide (or composition thereof) that is biostatic or biocidal against a target microbe. More specifically, an antimicrobially effective amount of peptide refers to an amount of peptide that inhibits the growth of, or is lethal to, a target microbe.

"Therapeutically Effective Amount" As used herein, "therapeutically effective amount" refers to an amount of peptide (or composition thereof) effective to ameliorate the symptoms of, or ameliorate, treat or prevent microbial infections or diseases related thereto in both plants and animals, including humans.

"Pharmaceutically Acceptable Salt:" As used herein, "pharmaceutically acceptable salt" refers to those salts which substantially retain the antimicrobial activity of the free bases and which are obtained by reaction with inorganic or organic acids.

5.2 Description of the Preferred Embodiments

The present invention provides antimicrobial protegrin peptides, compositions comprising the peptides, methods of using the peptides (or compositions thereof) to inhibit the growth of or kill a wide variety of microbial targets and methods of using the peptides (or compositions thereof) to treat or prevent microbial infections and diseases related thereto in both plants and animals.

Like the protegrin peptides described in U.S. Pat. No. 5,464,823; WO 95/03325; WO 95/37508; WO 97/18826 and WO 97/18827, each of which is incorporated herein in its entirety by reference, the protegrin peptides of the invention exhibit broad spectrum antimicrobial activity, being biostatic or biocidal against a wide range of microbial targets, including but not limited to, Gram-positive bacteria such as *L. monocytogenes, B. subtilis, E. faecalis* (including vancomycin-sensitive (VSEF) and vancomycin-resistant (VREF) strains), *E. faecium* (including vancomycin-sensitive (VSEF) and vancomycin-resistant (VREF) strains), *S. aureus* (including methicillin-sensitive (MSSA) and methicillin-resistant (MRSA) strains), *S. epidermis* (including methicillin-sensitive (MSSE) and methicillin-resistant (MRSE) strains), *S. salivarius, C. minutissium, C. pseudodiptheriae, C. stratium,* Corynebacterium group G1, Corynebacterium group G2, *S. pneumoniae* (including penicillin-resistant (PSRP) strains), *S. mitis* and *S. sanguis*; Gram-negative bacteria including *A. calcoaceticus, E. coli, K. pneumoniae, P. aeruginosa* ("Psa"), *S. marcescens, H. influenza,* Moraxella sp., *N. meningitidis, S. typhimurium, H. pylori, H. felis,* and *C. jejuni*; as well as protozoa, yeast and certain strains of viruses and retroviruses. Significantly, the peptides described herein are biostatic or biocidal against clinically relevant pathogens exhibiting multi-drug resistance such as, among others, vancomycin-resistant *Enterococcus faecium* or *faecalis* ("VRE"), penicillin-resistant *Streptococcus pneumoniae* ("PRSP") and methicillin-resistant *Staphylococcus aureus* ("MRSA").

Based on these activities, the peptides of the invention (or compositions thereof) are useful as biocidal or biostatic agents in a wide variety of applications. For example, the peptides can be used to disinfect or preserve a variety of materials including medical instruments, foodstuffs, medicaments, contact lens solutions, cosmetics and other nutrient-containing materials. The peptides of the invention are particularly useful as bacteriostatic or bactericidal agents against multi-drug-resistant pathogens such as VRE, MRSA and MSSE in a variety of clinical settings.

The peptides of the invention, or compositions thereof, are also useful for the prophylaxis or treatment of microbial infections and diseases related thereto in both plants and animals, including humans. Such diseases include, but are not limited to, Gram-negative and Gram-positive bacterial infections, endocarditis, pneumonia and other respiratory infections, urinary tract infections, systemic candidiasis, oral mucositis, etc.

It has been observed that several of the protegrin peptides, particularly native protegrin PG-1 (RGGRLCYCRRRFCVCVGR-NH$_2$; SEQ ID NO:1), are hemolytic against human red blood cells. As a consequence, some of the protegrin peptides are not optimal for systemic administration at concentrations which effect significant hemolysis.

Quite surprisingly, it has now been discovered that replacing one or more amino acid residues within the core structure of the protegrin peptides, namely the amino acids at positions 2, 3, 5, 7, 14 and/or 16, with a small amino acid, particularly an amino acid having a hydroxyl side chain, such as serine or threonine, exhibit significantly less hemolytic activity against human red blood cells than native protegrin PG-1. Moreover, it has also been discovered that further substituting at least one basic arginine in these analogues with a basic residue other than arginine, particularly with ornithine, lysine, 2,3-diaminobutyric acid, 2,4-diaminobutyric acid or mixtures thereof, increases the solubility and/or serum compatibility of the protegrin peptides. As a consequence of these observations, the protegrins of the invention are ideally suited for applications requiring increased solubility and/or intravenous administration.

5.2.1 The Peptides

The protegrin peptides of the invention are generally composed of about 10–30 amino acid residues and comprise a "core" structure having the amino acid sequence:

$$X_1\text{-}X_2\text{-}X_3\text{-}X_4\text{-}X_5\text{-}C_6\text{-}X_7\text{-}C_8\text{-}X_9\text{-}X_{10}\text{-}X_{11}\text{-}X_{12}\text{-}C_{13}\text{-}X_{14}\text{-}C_{15}\text{-}X_{16}\text{-}X_{17}\text{-}X_{18} \quad (I)$$

and its defined modified forms. Those peptides which may coincidentally occur in nature must be in a purified and/or isolated form or prepared synthetically or recombinantly.

The designation $X_n$ in each case represents an amino acid at the specified position in the peptide. Similarly, the designation $C_n$ represents an amino acid at the specified position, and further represents those positions in the amino acid sequence of formula (I) which may optionally contain amino acid residues capable of forming disulfide interlinkages.

The amino acid residues denoted by $X_n$ or $C_n$ may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

TABLE 1

Common Amino Acid Abbreviations

| Amino Acid | One-Letter Symbol | Commnon Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Ornithine | O | Orn |

TABLE 1-continued

Common Amino Acid Abbreviations

| Amino Acid | One-Letter Symbol | Commnon Abbreviation |
| --- | --- | --- |
| β-alanine | | bAla |
| 2,3-diaminopropionic acid | | Dpr |
| α-aminoisobutyric acid | | Aib |
| N-methylglycine (sarcosine) | | MeGly |
| Citrulline | | Cit |
| t-butylalanine | | t-BuA |
| t-butylglycine | | t-BuG |
| N-methylisoleucine | | MeIle |
| phenylglycine | | Phg |
| cyclohexylalanine | | Cha |
| Norleucine | | Nle |
| 1-naphthylalanine | | 1-Nal |
| 2-naphthylalanine | | 2-Nal |
| 4-chlorophenylalanine | | Phe (4-Cl) |
| 2-fluorophenylalanine | | Phe (2-F) |
| 3-fluorophenylalanine | | Phe (3-F) |
| 4-fluorophenylalanine | | Phe (4-F) |
| Penicillamine | | Pen |
| 1,2,3,4-tetrahydro-isoquinoline-3-carboxylic acid | | Tic |
| β-2-thienylalanine | | Thi |
| Methionine sulfoxide | | MSO |
| Homoarginine | | Har |
| N-acetyl lysine | | AcLys |
| 2,3-diaminobutyric acid | | Dab |
| 2,4-diaminobutyric acid | | Dbu |
| p-aminophenylalanine | | Phe (pNH$_2$) |
| N-methylvaline | | MeVal |
| Homocysteine | | hCys |
| Homoserine | | hSer |
| ε-amino hexanoic acid | | Aha |
| δ-amino valeric acid | | Ava |
| Hydroxyproline | | Hyp |
| Parabenzylphenylalanine | | Pba |
| Homophenylalanine | | hPhe |
| N-methylphenylalanine | | MePhe |

The protegrin peptides described herein are partially defined in terms of amino acid residues of designated classes. The amino acids are generally categorized into three main classes, hydrophilic amino acids, hydrophobic amino acids, and small amino acids, depending primarily on the characteristics of the amino acid side chain. These main classes are further divided into subclasses. Hydrophilic amino acids include amino acids having acidic, basic or polar side chains and hydrophobic amino acids include amino acids having aromatic or apolar side chains. As will be discussed more thoroughly below, the class of small amino acids includes amino acids having either polar or apolar side chains, but wherein the side chain does not contribute significantly to the net properties of the peptide. The definitions of the classes of amino acids as used herein are as follows:

"Hydrophobic Amino Acid" refers to an amino acid having a side chain that is uncharged at physiological pH and that is repelled by aqueous solution so as to seek the inner positions in the conformation of a peptide in which it is contained when the peptide is in aqueous medium.

"Aromatic Amino Acid" refers to a hydrophobic amino acid having a side chain containing at least one ring having a conjugated π-electron system (aromatic group). Genetically encoded aromatic amino acids include phenylalanine, tyrosine and tryptophan. Non-genetically encoded aromatic amino acids include phenylglycine, 2-naphthylalanine, β-2-thienylalanine, 1,2,3,4-tetrahydroisoquinoline-3-carboxylic acid, 4-chloro-phenylalanine, 2-fluorophenylalanine, 3-fluorophenylalanine and 4-fluorophenylalanine.

"Apolar Amino Acid" refers to a hydrophobic amino acid having a side chain that is uncharged at physiological pH. Genetically encoded apolar amino acids include leucine, valine, isoleucine and methionine. Non-genetically encoded apolar amino acids include t-butylalanine, t-butylglycine, N-methylisoleucine, norleucine, N-methyl valine and cyclohexylalanine.

"Hydrophilic Amino Acid" refers to an amino acid having a side chain that is attracted by aqueous solution so as to seek the surface positions in the conformation of a peptide in which it is contained when the peptide is in aqueous medium at physiological pH.

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include the non-cyclic amino acids arginine and lysine and the cyclic amino acid histidine. Non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but that is not sufficiently repelled by aqueous solutions so as to seek inner positions in the conformation of a peptide in which it is contained when the peptide is in aqueous medium. Genetically encoded polar amino acids include asparagine and glutamine. Non-genetically encoded polar amino acids include citrulline, N-acetyl lysine and methionine sulfoxide.

"Small Amino Acid" refers to an amino acid having a side chain which is not sufficiently large to confer significant hydrophobicity or hydrophilicity to the peptide. Small amino acids are those with side chains having four or fewer carbons when the side chain contains at least one polar group, and three or fewer carbons when the side chain does not contain a polar group. Genetically encoded small amino acids include glycine, serine, alanine and threonine. The gene-encoded secondary imino acid proline is also designated as a small amino acid, although it is known to affect the secondary conformation of peptide chains. Non-genetically encoded small amino acids include β-alanine, N-methyl glycine (sarcosine) and α-aminoisobutyric acid.

"Cysteine-Like Amino Acid" refers to an amino acid having a side chain capable of participating in a disulfide linkage. Thus, cysteine-like amino acids generally have a side chain containing at least one thiol (SH) group. Genetically encoded cysteine-like amino acids include cysteine. Non-genetically encoded cysteine-like amino acids include homocysteine and penicillamine.

As will be appreciated by those having skill in the art, the degree of attraction or repulsion required for classification as polar, apolar or small is somewhat arbitrary. For example, while both serine and threonine contain polar hydroxyl groups these residues are classified as small amino acids, as their side chains do not confer significant overall hydrophilicity to the peptides of the invention. Amino acids not specifically named herein can be readily classified into the above-defined categories on the basis of known behavior as compared with amino acids specifically identified.

Certain commonly encountered amino acids which are not genetically encoded of which the peptides of the invention may be composed include, but are not limited to, β-alanine (b-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 1-naphthylalanine (1-Nal); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (Har); N-acetyl lysine (AcLys); 2,3-diaminobutyric acid (Dab); 2,4-diaminobutyric acid (Dbu); p-aminophenylalanine (Phe(pNH$_2$)); N-methyl valine (MeVal); homocysteine (hCys), hydroxyproline (Hyp), para-benzyl phenylalanine (Pba), homophenylalanine (hPhe), N-methyl phenylalanine (MePhe) and homoserine (hSer). These amino acids also fall conveniently into the categories defined above.

Other amino acids which can be used in conjunction of the invention are well-known in the art, and can be found, e.g., in Fasman, 1989, *Practical Handbook of Biochemistry and Molecular Biology*, CRC Press, Boca Raton, Fla., pp. 3–76 and references cited therein.

The classifications of the above-described genetically encoded and non-encoded amino acids are summarized in TABLE 2, below. It is to be understood that TABLE 2 is for illustrative purposes only and does not purport to be an exhaustive list of amino acid residues that may comprise the cyclic peptides described herein.

TABLE 2

Common Amino Acid Classifications

| Classification | Genetically Encoded | Non-Genetically Encoded |
| --- | --- | --- |
| Hydrophobic | | |
| Aromatic | F, Y, W | Phg, 1-Nal, 2-Nal, Thi, Tic, Phe (4-Cl), Phe(2-F), Phe (3-F), Phe (4-F) |
| Apolar | L, V, I, M | t-BUA, t-BUG, MeIle, Nle, MeVal, Cha |
| Hydrophilic | | |
| Acidic | D, E | |
| Basic | H, K, R | Dpr, Orn, Har, Phe (p-NH$_2$), Dab, Dbu |
| Polar | Q, N | Cit, AcLys, MSO |
| Small | S, T, G, A, P | bAla, MeGly, Aib, hSer |
| Cysteine-Like | C | Pen, hCys |

In the peptides of formula I, the symbol "—" between amino acid residues $X_n$ and/or $C_n$ generally designates a backbone interlinkage. Thus, the symbol "—" usually designates an amide linkage (—C(O)—NH—). It is to be understood, however, that in all of the peptides of the invention one or more amide linkages may optionally be replaced with a linkage other than amide. Such linkages include, but are not limited to, isosteres of amide, substituted amides (—C(O)NR—, where R is $C_1$–$C_6$ alkyl or $C_5$–$C_{20}$ aryl), —CH$_2$NH—, —CH$_2$S—, —CH$_2$CH$_2$, —CH=CH— (cis and trans), —C(O)CH$_2$—, —CH(OH)CH$_2$— and —CH$_2$SO—. Thus, as used herein, "peptides" refers not only to compounds having a peptide backbone, but also compounds wherein one or more amide linkages is replaced with the above-described linkages.

Peptides having such linkages and methods for preparing such peptides are well-known in the art (see, e.g., Spatola, 1983, *Vega Data* 1(3) (general review); Spatola, 1983, "Peptide Backbone Modifications" In: *Chemistry and Biochemistry of Amino Acids Peptides and Proteins* (Weinstein, ed.), Marcel Dekker, New York, p. 267 (general review); Morley, 1980, *Trends Pharm. Sci.* 1:463–468; Hudson et al., 1979, *Int. J. Prot. Res.* 14:177–185 (—CH$_2$NH—, —CH$_2$CH$_2$—); Spatola et al., 1986, *Life Sci.* 38:1243–1249 (—CH$_2$—S); Hann, 1982, *J. Chem. Soc. Perkin Trans. I.* 1:307–314 (—CH=CH—, cis and trans); Almquist et al., 1980, *J. Med. Chem.* 23:1392–1398 (—COCH$_2$—); Jennings-White et al., *Tetrahedron. Lett.* 23:2533 (—COCH$_2$—); European Pat. Application EP 45665 (1982) CA:97:39405 (—CH(OH)CH$_2$—); Holladay et al., 1983, *Tetrahedron Lett.* 24:4401–4404 (—C(OH)CH$_2$—); and Hruby, 1982, *Life Sci.* 31:189–199 (—CH$_2$—S—)

Generally, the peptides of the invention are composed of about 10 to 30 amino acid residues. Thus, it is to be understood that while formula (I) designates eighteen specified amino acid positions comprising the "core" peptide structure, the peptides of the invention may contain fewer than, or greater than, 18 amino acid residues without deleteriously affecting, and in some cases even enhancing, the antimicrobial or other useful properties of the peptides. For peptides containing fewer than 18 amino acid residues, certain specified amino acids are not present within the peptide sequence, as will be discussed in more detail below. For peptides containing greater than 18 amino acid residues, the amino acid sequence shown as formula (I) may contain extensions at the N- and/or C-terminus of additional amino acid residues or peptide sequence. It is to be understood that such additional amino acid residues or peptide sequences are non-interfering in that they will not significantly deleteriously affect the antimicrobial activity of the peptide as compared with naturally occurring protegrins.

The peptides of the invention are characterized by a "core" structure containing two main elements or motifs: a reverse-turn region bracketed by two strands that form an anti-parallel β-sheet. While not intending to be bound by theory, it is believed that the antimicrobial activity of the compounds of formula (I) is in part associated with such a core structure.

The β-sheet region of the peptides comprises an N-strand (residues $X_1$–$C_8$) and a C-strand (residues $C_{13}$–$X_{18}$). The N-strand and C-strand are arranged anti-parallel to one another and are non-covalently linked together via backbone-backbone hydrogen bonds (for a detailed description of the structure of β-sheets the reader is referred to Creighton, 1993, *Protein Structures and Molecular Properties*, W. H. Freeman and Co., New York, and references cited therein). While not intending to be bound by theory, it is believed that the most important residues comprising the β-sheet region are residues $X_5$–$C_8$ and $C_{13}$–$X_{16}$.

Preferably, the β-sheet region of the peptides is amphiphilic, i.e., one surface of the β-sheet has a net hydrophobic character and the other surface has a net hydrophilic character. When two strands of an L- or D-peptide are arranged in an antiparallel β-sheet, the side chains of amino acid residues that are adjacent to one another intrastrand-wise point in opposite directions so as to be positioned on opposite surfaces of the β-sheet. The side chains of amino acid residues adjacent to one another interstrand-wise point in the same direction so as to be positioned on the same surface of the β-sheet (see, e.g., FIG. 6 of WO 97/18826). Using this general structural motif, an amphiphilic antiparallel β-sheet is obtained by selecting amino acids at each residue position so as to yield a β-sheet having hydrophobic side chains positioned on one surface of the sheet and hydrophilic side chains positioned on the other.

Of course, it will be appreciated that as the surfaces of the amphiphilic anti-parallel β-sheet region need only have net hydrophobic or net hydrophilic character, each side chain comprising a particular surface need not be hydrophobic or hydrophilic. The surfaces may contain side chains that do not significantly alter the net character of the surface. For example, both the hydrophobic and hydrophilic surfaces may contain small amino acid side chains, as these side chains do not significantly contribute to the net character of the surface.

The β-sheet region of the peptides of formula I may contain from one to four cysteine-like amino acids, designated $C_6$, $C_8$, $C_{13}$ and $C_{15}$, which may participate in interstrand disulfide bonds. Peptides of the invention that contain at least two cysteine-like amino acid residues may be in straight-chain or cyclic form, depending on the extent of disulfide bond formation. The cyclic forms are the result of the formation of disulfide linkages among all or some of the four invariant cysteine-like amino acids. Cyclic forms of the invention include all possible permutations of disulfide bond formation. The straight-chain forms are convertible to the cyclic forms, and vice versa. Methods for forming disulfide bonds to create the cyclic forms are well known in the art, as are methods to reduce disulfides to form the linear compounds.

The naturally occurring protegrins (PG-1 through PG-5) contain two disulfide bonds; one between cysteines $C_6$–$C_{15}$ and another between cysteines C8–$C_{13}$ (Harwig et al., 1995, *J. Peptide Sci.* 3:207). Accordingly, in those embodiments having two disulfide linkages, forms having disulfide linkages between $C_6$–$C_{15}$ and $C_8$–$C_{13}$ are preferred. Such peptides are designated "native" forms. However, it has been found that forms of the protegrins containing only one disulfide linkage are active and easily prepared. Preferred among embodiments having only one disulfide linkage are those represented by $C_6$–$C_{15}$ alone and by $C_8$–$C_{13}$ alone.

Forms containing a $C_6$–$C_{15}$ disulfide as the only disulfide linkage are generally designated "bullet" forms of the protegrins; those wherein the sole disulfide is $C_8$–$C_{13}$ are designated the "kite" forms. The bullet and kite forms can most conveniently be made by replacing each of the cysteine-like amino acid residues at the positions that are not involved in a disulfide linkage with amino acids that do not participate in disulfide bonds, preferably with small amino acids such as glycine, serine, alanine or threonine. Alternatively, $C_8$ and/or $C_{13}$ may be absent.

As the linearized or "snake" forms of the native peptides have valuable activities, the peptides of the invention include linearized forms wherein the sulfhydryl (SH) groups are chemically stabilized with suitable reagents. As defined herein, "SH-stabilized" forms of the peptides of the invention contain sulfhydryl groups that have been reacted with standard reagents to prevent reformation of disulfide linkages or forms wherein the cysteine-like amino acid residues are replaced by other amino acids as set forth above. It is preferred that all four cysteine-like amino acid residues be replaced or SH-stabilized in order to minimize the likelihood of the formation of intermolecular disulfide linkages.

The sulfur atoms involved in an interstrand disulfide bridge in a β-sheet are not positioned within the plane defined by the interstrand backbone-backbone hydrogen-bonds; the sulfur atoms are at an angle with respect to the β-carbons of the bridged amino acid residues so as to be positioned on a surface of the β-sheet. Thus, the sulfur atoms of the disulfide linkages contribute to the net hydrophilicity of a surface of the β-sheet. It is to be understood that in the peptides of formula I a β-sheet region defined by the following formula is specifically contemplated to fall within the definition of amphiphilic antiparallel sheet as described herein:

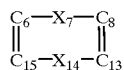

wherein $C_6$, $C_8$, $C_{13}$ and $C_{15}$ are each independently a cysteine-like amino acid, $X_7$ and $X_{14}$ are each independently a hydrophobic or small amino acid and ‖ is a disulfide bond. In a particularly preferred embodiment, $C_6$, $C_8$, $C_{13}$ and $C_{15}$ are each cysteine.

Those having skill in the art will recognize that substituting an L-amino acid with its corresponding D-enantiomer at a specific residue position of a peptide may disrupt the structural stability and/or amphiphilicity of the amphiphilic anti-parallel β-sheet region of the peptide. The degree to which any particular enantiomeric substitution disrupts the structural stability or amphiphilicity depends, in part, on the size of the amino acid side chain and position of the residue within the β-sheet. Preferably, the β-sheet region of the peptides of formula I will contain mixtures of L- and D-amino acids that do not significantly affect the stability or amphiphilicity of the β-sheet region as compared to peptides containing the corresponding all D- or all L-enantiomeric forms of the sheet. Enantiomeric substitutions that do not substantially affect the stability or amphiphilicity of the β-sheet region will be readily apparent to those having skill in the art.

In a preferred embodiment of the invention, hydrophobic, basic, polar and cysteine-like amino acids comprising the β-sheet region are either all L-enantiomers or all D-enantiomers. Small amino acids comprising the β-sheet region may be either L-enantiomers or D-enantiomers.

The reverse-turn region of the peptides of formula I (residues $X_9$-$X_{10}$-$X_{11}$-$X_{12}$ taken together) links the strands of the anti-parallel β-sheet. Thus, the reverse-turn region comprises a structure that reverses the direction of the polypeptide chain so as to allow a region of the peptide to adopt an anti-parallel β-sheet secondary structure.

The reverse-turn region of the peptides generally comprises two, three or four amino acid residues (residue $X_9$ and/or $X_{12}$ may be absent). An important feature of the peptides of the invention is the presence of a positive charge in the turn region of the molecule. Thus, one of $X_9$–$X_{12}$, and preferably two of $X_9$–$X_{12}$, must be basic amino acids. Such two, three and four amino acid segments capable of effecting a turn in a peptide are well known and will be apparent to those of skill in the art.

In a preferred embodiment of the invention, the reverse-turn is a three amino acid residue γ-turn. Virtually any γ-turn sequence known in the art may be used in the peptides of the invention, including those described, for example, in Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol* 206:759–777; and Tramontano et al., 1989, *Proteins: Struct. Funct. Genet.* 6:382–394.

In another preferred embodiment the reverse-turn is a four amino acid residue β-turn. In such structures, the two internal amino acid residues of the turn are usually not involved in the hydrogen-bonding of the anti-parallel β-sheet; the two amino acid residues on either side of the internal residues are usually included in the hydrogen-bonding of the β-sheet. While not intending to be bound by theory, it is believed that such hydrogen bonding helps stabilize the β-sheet region of the molecule.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, *Adv. Protein Chem.* 34:167–339; Rose et al., 1985, *Adv. Protein Chem.* 37:1–109; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394). All of these types of peptide β-turn structures and their corresponding sequences, as well as later discovered peptide β-turn structures and sequences, are specifically contemplated by the invention.

The specific conformations of short peptide turns such as β-turns depend primarily on the positions of certain amino acid residues in the turn (usually Gly, Asn or Pro). Generally, the type-I β-turn is compatible with any amino acid residue at positions $X_9$ through $X_{12}$, except that Pro cannot occur at position $X_{11}$. Gly predominates at position $X_{12}$ and Pro predominates at position $X_{10}$ of both type-I and type-II turns. Asp, Asn, Ser and Cys residues frequently occur at position $X_9$, where their side chains often hydrogen-bond to the NH of residue $X_{11}$.

In type-II turns, Gly and Asn occur most frequently at position $X_{11}$, as they adopt the required backbone angles most easily. Ideally, type-I' turns have Gly at positions $X_{10}$ and $X_{11}$, and type-II' turns have Gly at position $X_{10}$. Type-III turns generally can have most amino acid residues, but type-III' turns usually require Gly at positions $X_{10}$ and $X_{11}$.

Type-VIa and VIb turns generally have a cis peptide bond and Pro as an internal residue. For a review of the different types and sequences of β-turns in proteins and peptides the reader is referred to Wilmot et al., 1988, *J. Mol. Biol.* 203:221–232.

Preferred β-turn sequences are as follows (listed in the order $X_9$ to $X_{12}$): ZZZG; ZZZF; ZZZY; ZZSG; ZZAL; ZGZL; ZXZF; ZFZL; ZPZV; ZPZF; ZGZY; ZGZF; IZGZ; LZZF; YZZY; ZZZE; YZZV; YZGZ, wherein X is MeGly and each Z is independently an L- or D-enantiomer of R, K, Dab, Dbu or Orn.

Additional preferred β-turns include those wherein $X_{10}$ and/or $X_{11}$ are Tic or Hyp, as these residues are known to effect or induce β-turn structures in peptides and proteins.

The peptides of the invention are generally basic, i.e., they have a net positive charge at physiological pH. While not intending to be bound by theory, it is believed that the presence of positively charged amino acid residues, particularly in the turn region of the molecule, is important for antimicrobial activity.

It is understood that in a statistical collection of individual amino acid residues in a structure such as a peptide some of the amino acid residues will be positively charged, some negatively charged and some uncharged. Thus, some of the peptides will have a charge and some not. To fit the definition of "basic," an excess of amino acid residues in the peptide molecule are positively charged at physiological pH. Thus, approximately 15% but no more than up to about 50% of the amino acids must be basic amino acids, and the compounds must have a net charge of at least +1 at physiological pH. Preferably, the peptides of the invention will have a net charge of at least +3 at physiological pH.

For embodiments having as few as 10 amino acids, there may be only one basic amino acid residue; however, at least two basic residues, even in this short-chain residue, are preferred. If the protegrin peptide contains as many as 15 amino acid residues, two basic residues are required. It is preferred that at least 20% of the amino acids in the sequence be basic, with 30% basic amino acids being particularly preferred.

Two significant features of the protegrins of the invention are their increased solubility and compatibility in physiological solutions, including serum, and reduced hemolytic activity against human red blood cells, as compared with native protegrin PG-1. While not intending to be bound by any particular theory, it is believed that these properties are conferred by the presence of one or more hydroxyl-containing amino acids at certain invariant positions (positions 2, 3, 5, 7, 14 and/or 16) of the core structure of the protegrins described herein. By "hydroxyl-containing amino acid" is meant an amino acid having a side chain which contains at least one hydroxyl group, such as serine and threonine. Increased serum compatibility is thought, in part, to also be due to the replacement of at least one basic arginine residue in these threonine analogues with other basic residues, particularly lysine, ornithine, 2,3-diaminobutyric acid and/or 2,4-diaminobutyric acid.

The amino terminus of the peptides of the invention may be in the free amino form, or may be acylated by a group of the formula RC(O)—, wherein R represents an aryl group of 5–20 C, (preferably 6–10 C), a heteroaryl group of 5–20 atoms (preferably 5–10 atoms) or a hydrocarbyl group of 1–25C (preferably 1–10C, more preferably 1–8C). The hydrocarbyl group can be saturated or unsaturated, straight chain, branched or cyclic, and is typically, for example, methyl, ethyl, isopropyl, t-butyl, n-pentyl, cyclohexyl, cyclohexene-2-yl, hexene-3-yl, hexyne-4-yl, octyl, decyl, eicanosyl and the like, with octyl being preferred.

Also included within the definition of "N-terminal acylated" are those peptides wherein the side chain amino group of an N-terminal basic residue is acylated with a group of the formula RC(O)— as described above. The side-chain amino group may be acylated in addition to, or instead of, the N-terminal amine. A particularly convenient means for introducing aromatic or heteroaromatic groups at the side chain amino group is acylating the side chain amino group with an amino acid having an aromatic or heteroaromatic side chain, such as W.

Alternatively, the N-terminus may contain aromatic groups such as naphthalene, etc. Such groups may be conveniently incorporated into the peptides of the invention by using amino acids such as 1-naphthylalanine or 2-naphthylalanine as the N-terminal amino acid residue.

The N-terminus of the peptides may also be substituted to use solute-specific transmembrane channels to facilitate their entry into the bacterial periplasm. For example, the N-terminus may be conveniently modified with catechol using catechol-NHS activated ester.

The C-terminus of the peptides may be in the form of the underivatized carboxyl group, either as the free acid or an acceptable salt, such as the potassium, sodium, calcium, magnesium, or other salt of an inorganic ion or of an organic ion such as caffeine. In some embodiments, it is difficult to make salts since the remainder of the molecule bears a positive charge which may repel the relevant cation. The carboxyl terminus may also be derivatized by formation of an ester with an alcohol of the formula ROH, or may be amidated by an amine of the formula $NH_3$, or $RNH_2$, or $R_2NH$, wherein each R is independently aryl, heteroaryl or hydrocarbyl as defined above. Amidated forms of the peptides wherein the C-terminus has the formula —C(O)$NH_2$ are preferred.

Addition of lipophilic groups at the C- and/or N-terminus facilitates the transition of the peptide into the membrane of the target microbe and penetration into sites of infection. Choice of optimum substitution is determined by evaluation with respect to the lipid content of the target microbe.

Thus, in one illustrative embodiment, the invention provides antimicrobial protegrin peptides composed of about 10–30 amino acid residues which comprise the amino acid sequence:

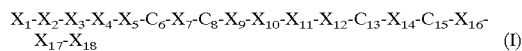

$$X_1\text{-}X_2\text{-}X_3\text{-}X_4\text{-}X_5\text{-}C_6\text{-}X_7\text{-}C_8\text{-}X_9\text{-}X_{10}\text{-}X_{11}\text{-}X_{12}\text{-}C_{13}\text{-}X_{14}\text{-}C_{15}\text{-}X_{16}\text{-}X_{17}\text{-}X_{18} \quad (I)$$

or a pharmaceutically acceptable salt or N-terminal acylated or C-terminal amidated or esterified form thereof, wherein:

each of $C_8$ and $C_{13}$ is independently present or not present, and if present each is independently a cysteine-like, basic, small, polar or hydrophobic amino acid;

each of $C_6$ and $C_{15}$, is independently a cysteine-like, basic, small, polar or hydrophobic amino acid;

each of $X_1$, $X_2$, $X_3$, $X_4$ and $X_5$ is independently present or not present, and if present each is independently a basic, hydrophobic, polar or small amino acid;

each of $X_7$ and $X_{14}$ is independently a hydrophobic or a small amino acid;

each of $X_9$ and $X_{12}$ is independently present or not present;

$X_9$–$X_{12}$ taken together are capable of effecting a reverse turn when contained in the amino acid sequence of formula (I) and at least one of $X_9$–$X_{12}$ must be a basic amino acid;

each of $X_{16}$, $X_{17}$ and $X_{18}$ is independently present or not present, and if present each is independently a basic, hydrophobic, polar or small amino acid; and at least about 15% up to about 50% of the amino acids comprising said antimicrobial peptide are basic amino acids such that said antimicrobial peptide has a net charge of at least +1 at physiological pH, with the proviso that at least one of $X_2$, $X_3$, $X_5$, $X_7$, $X_{14}$ or $X_{16}$ must be a small amino acid, preferably a hydroxyl-containing amino acid, such as S or T.

The invention peptides can be further illustrated by way of preferred embodiments. In one set of preferred embodiments, all of the cysteine-like amino acid residues at positions $C_6$, $C_8$, $C_{13}$ and $C_{15}$ are present as are $X_9$ and $X_{12}$.

In another set of preferred embodiments, $X_1$, $X_2$, $X_3$ and $X_4$ are each not present.

In another set of preferred embodiments, at least one, and preferably two, of $X_1$, $X_2$, $X_3$ and $X_4$ are hydrophobic amino acids, preferably I, V, L, Y, F or W.

In another set of preferred embodiments, $X_9$–$X_{12}$ contain at least one hydrophobic amino acid residue, preferably Phe, Tyr or Trp.

In yet another set of preferred embodiments, each of $X_1$ and $X_9$ is independently selected from the group consisting of R, K, Orn, Dab, Dbu and Har or hydrophobic; preferably $X_1$ is R, K, Har and $X_9$ is R, K, Har or hydrophobic, especially I, V, L, W, F or Y.

In still another set of preferred embodiments, each of $X_2$ and $X_3$ is independently selected from the group consisting of G, A, S, T, I, V, L, F, Y and W; more preferably, $X_2$ and $X_3$ are G, W, F, Y, L, or V; however, $X_2$ and/or $X_3$ may be absent.

In another set of preferred embodiments, $X_4$ is selected from the group consisting of R, K, H, Orn, Har, Dab, Dbu, G, A, S, T, F, Y and W; more preferably, $X_4$ is R, K, Orn, Dab, Dbu, G or W.

In another set of preferred embodiments, each of $X_5$ and $X_{16}$ is independently selected from the group consisting of I, V, L, Nle, W, Y, and F, preferably I, V, L, W, F and Y. However, $X_5$ and/or $X_{16}$ may be absent.

In another set of preferred embodiments, each of $X_7$ and $X_{14}$ is independently selected from the group consisting of I, V, L, W, Y and F; preferably $X_7$ is I, F, Y or W and $X_{14}$ is I, V, L, W, Y, or F.

In another set of preferred embodiments, $X_9$ is R, K, H, Orn, Dab, Dbu, Har, I, V, L, Nle, W, Y or F, and $X_{12}$ is I, L, V, W, F or Y; more preferably an aromatic amino acid such as Y, W, or F.

In another set of preferred embodiments, $X_{10}$ is R, Orn, Dab, Dbu, G, W or P.

In another set of preferred embodiments, $X_{11}$ is R, K, Orn, Dab, Dbu, G, W or P.

In another set of preferred embodiments, $X_{17}$ is absent, but when present, is G, A, S or T;

In another set of preferred embodiments, $X_{18}$ is absent, but when present, is R, K, H, Orn, Dab, Dbu or Har.

In another set of preferred embodiments, $X_1$, $X_2$, $X_3$ and $X_4$ are each present, $X_1$ and $X_4$ are basic and $X_2$ and $X_3$ are small or hydrophobic. Preferred embodiments of $X_1$–$X_4$ include R-G-G-R, R-G-W-R, R-L-L-R and the like.

Preferred embodiments for the basic amino acid to replace cysteine-like residues are R, K, H, Orn, Dab, Dbu and Har, most preferably R, K or Orn. Preferred small amino acids to replace the cysteine-like residues include G, A, S and T, most preferably A and T.

In another set of preferred embodiments, the peptides of formula (I) are composed of 10–18 amino acid residues.

In another set of preferred embodiments, $X_7$ and $X_{14}$ are each independently S or T.

In another set of preferred embodiments, $X_1$, $X_2$ and $X_3$ are each absent.

In another set of preferred embodiments, $X_{17}$ and $X_{18}$ are each absent.

In still another set of preferred embodiments, the peptides of formula (I) are defined as follows:

$X_1$ is absent or a basic amino acid;
$X_2$ is absent or a basic or small amino acid;
$X_3$ is absent, G or T;
$X_4$ is a basic amino acid, T or W;
$X_5$ is F, L, Y, K, Q or T;
$C_6$ is Cys or H;
$X_7$ is F, L, Y, S or T;
$C_8$ is Cys;
$X_9$ is a basic amino acid or Y;
$X_{10}$ is a basic amino acid, G or MeGly;
$X_{11}$ is a basic amino acid;
$X_{12}$ is F, Y, V or E;
$C_{13}$ is Cys;
$X_{14}$ is V, T or S;
$C_{15}$ is absent or Cys;
$X_{16}$ is absent, V, Y, F, E or T;
$X_{17}$ is absent or G; and/or
$X_{18}$ is absent, Orn or R.

In yet another set of preferred embodiments, the N-terminal amino acid is Lys which is acylated at the $\epsilon$-amino group with R—C(O)—, where R is $C_1$–$C_8$ alkyl, $C_6$–$C_{10}$ aryl or $C_6$–$C_{10}$ heteroaryl.

In another set of preferred embodiments, at least one basic residue is other than R. More preferably, two or more basic residues are other than R.

Particularly preferred protegrin peptides according to the invention are the bullet, kite and snake forms of the following peptides:

| | | |
|---|---|---|
| [³T]PG-1: | RGTRLCYCRRRFCVCVGR | (SEQ ID NO:2) |
| [⁵T]PG-1: | RGGRTCYCRRRFCVCVGR | (SEQ ID NO:3) |
| | OGGOTCYCOOOFCVCVGO | (SEQ ID NO:4) |
| [⁷T]PG-1: | RGGRLCTCRRRFCVCVGR | (SEQ ID NO:5) |
| [¹⁴T]PG-1: | RGGRLCYCRRRFCTCVGR | (SEQ ID NO:6) |
| | OGGOLCYCOOOFCTCVGO | (SEQ ID NO:7) |
| [¹⁶T]PG-1: | RGGRLCYCRRRFCVCTGR | (SEQ ID NO:8) |
| | OGGOLCYCOOOFCVCTGO | (SEQ ID NO:9) |
| | OTT LCYCOGOFCVCVGO | (SEQ ID NO:10) |
| | OTOLCYCOZOPCVCV | (SEQ ID NO:11) |
| | XTXLCYCXXXFCTCV | (SEQ ID NO:12) |
| | XTXOCYCXXXYCTCV | (SEQ ID NO:13) |
| | WTCYCOOOFCVCV | (SEQ ID NO:14) |
| | JTCYCOOOFCVCV | (SEQ ID NO:15) |
| | JLCFCOOOFCTCV | (SEQ ID NO:16) |
| | JTCFCOOOFCTCV | (SEQ ID NO:17) |
| | HTHLCYXXVCV | (SEQ ID NO:18) | and the N-terminal acylated and C-terminal amidated or esterified forms thereof, wherein J is N-$\epsilon$-tryptophanyl-Lysine, X is Dbu and Z is MeGly. C-terminal amidated forms of the above peptides are most preferred.

Another set of particularly preferred protegrins according to the invention are SEQ ID NOS:12, 13 and 18, in either the C-terminal acid or amidated forms, that are acylated at the N-terminus, preferably with $C_8H_{18}$—C(O)—.

5.2.2 Identification of Active Protegrins

Generally, active protegrin peptides of the invention are identified using in vitro screening assay. Indeed, in many instances the protegrin peptides of the invention will be used in vitro as preservatives, topical antimicrobial treatments, etc. Additionally, despite certain apparent limitations of in vitro susceptibility tests, clinical data indicate that a good correlation exists between minimal inhibitory concentration (MIC) test results and in vivo efficacy of antibiotic compounds (Murray, 1994, *Antimicrobial Susceptibility Testing*, Poupard et al., eds., Plenum Press, NY; Knudsen et al., 1995, *Antimicrob. Agents Chemother.* 39(6):1253–1258). Thus, protegrin peptides useful for treating infections and diseases related thereto are also conveniently identified by demonstrated in vitro antimicrobial activity against specified microbial targets.

Generally, the in vitro antimicrobial activity of antimicrobial agents is tested using standard NCCLS bacterial inhibition assays, or MIC tests (see, National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically—Third Edition," Approved Standard M7-A3, National Committee for Clinical Standards, Villanova, Pa). It has been discovered, however, that these standard NCCLS MIC assays do not work well for identifying active peptides of the invention. Thus, preferably the compounds are screened using the modified NCCLS MIC assay and other assays described in WO 97/18826 and/or in Steinberg et al., 1997, *Antimicrobial Agents and Chemotherapy* 41(8):1738–1742.

It will be appreciated that other assays that are well known in the art, or that will become apparent to those having skill in the art upon review of this disclosure, may also be used to identify active protegrin peptides of the invention. Such assays include, for example, the assay described in Lehrer et al., 1988, *J. Immunol. Methods* 108:153 and Steinberg and Lehrer, "Designer Assays for Antimicrobial Peptides: Disputing the 'One Size Fits All' Theory," In: *Antibacterial Peptide Protocols*, Shafer, Ed., Humana Press, New Jersey.

Generally, active peptides of the invention will exhibit MICs (as measured using the modified NCCLS assays described in WO 97/18826) of less than about 64 μg/mL, usually less than about 32 μg/mL, preferably less than about 16 μg/mL and most preferably less than about 4 μg/mL.

5.2.3 Preparation of the Peptides

5.2.3.1 Chemical Synthesis

The protegrin peptides of the invention may be prepared using virtually any art-known technique for the preparation of cyclic peptides. For example, the peptides may be prepared in linear or non-cyclized form using conventional solution or solid phase peptide syntheses and cyclized using standard chemistries.

Standard methods for the chemical synthesis of peptides of the sizes described herein are known. Most commonly used currently are solid phase synthesis techniques; indeed, automated equipment for systematically constructing peptide chains can be purchased. Solution phase synthesis can also be used and has considerable benefits for large scale production. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group at the amino terminus. Methods for acetylating or, more generally, acylating, the free amino group at the N-terminus are generally known in the art; in addition, the N-terminal amino acid may be supplied in the synthesis in acylated form.

At the carboxyl terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. However, when the compound of formula (I) contains a multiplicity of basic residues, salt formation may be difficult or impossible. The carboxyl terminus may also be esterified using alcohols of the formula ROH wherein R is aryl, heteroaryl or hydrocarbyl as previously defined. Similarly, the carboxyl terminus may be amidated so as to have the formula —$CONH_2$, —CONHR, or —$CONR_2$, wherein each R is independently aryl, heteroaryl or hydrocarbyl as previously defined. Techniques for esterification and amidation as well as neutralizing in the presence of base to form salts are all standard organic chemical techniques.

If the peptides of the invention are prepared under physiological conditions, the side-chain amino groups of any basic amino acids will be in the form of the relevant acid addition salts.

For synthesis of linear peptide with a C-terminal amide, the peptide sequence is conveniently synthesized on a Fmoc Rink amide solid support resin (Bachem) using Fmoc chemistry on an automated ABI 433 peptide synthesizer (ABD, Perkin Elmer, Foster City, Calif.) according to the manufacturer's standard protocols. Cleavage is typically carried out in 10 ml of thioanisole/EDT/TFA (1/1/9) for 2 hours at room temperature. Crude cleavage product is precipitated with t-butyl methyl ether, filtered and dried.

Peptides containing an N-terminal basic amino acid acylated at the side chain amino group are conveniently prepared using appropriately protected and acylated amino acids. Suitable amino acids are available from Bachem or can be readily prepared using standard techniques.

Formation of disulfide linkages, if desired, is conducted in the presence of mild oxidizing agents. Chemical oxidizing agents may be used, or the compounds may simply be exposed to the oxygen of the air to effect these linkages. Various methods are known in the art. Processes useful for disulfide bond formation have been described by Tam et al., *Synthesis* (1979) 955–957; Stewart et al., *Solid Phase Peptide Synthesis*, 2d Ed. Pierce Chemical Company Rockford, Ill. (1984); Ahmed et al., 1975, *J. Biol. Chem.* 250:8477–8482 and Pennington et al., *Peptides* 1990, Giralt et al., ESCOM Leiden, The Netherlands (1991) 164–166. An additional alternative is described by Kamber et al., 1980, *Helv. Chim. Acta* 63:899–915. A method conducted on solid supports is described by Albericio, 1985, *Int. J. Pest. Protein. Res.* 26:92–97.

A particularly preferred method is solution oxidation using molecular oxygen. This method has been used to refold synthetic protegrins PG-1, PG-3 in its amide or acid forms, enantio PG-1 and the two unidisulfide PG-1 compounds ($C_6$–$C_{15}$ and $C_8$–$C_{13}$). Recoveries are as high as 65–90%.

In this preferred method to form disulfide linkages, the crude peptide is dissolved in DMSO and added to 20 mM ammonium acetate buffer, pH 7. The final concentration of the peptide in the solution is between 1–8 mg/ml, the pH ranges from 7.0–7.2, and the DMSO concentration ranges from 5–20%. The peptide solution is stirred overnight at room temperature.

The pH of the solution is adjusted to pH5 with concentrated acetic acid and the sample purified on Prep LC. After loading, the column is washed with 10% acetonitrile/$H_2O$ (0.1% TFA) until the UV absorbance decreases to the baseline. The gradient is then started.

Column: Vydac Cat#218TP101522, 2.2×25 cm, $C_{18}$ peptides & proteins; UVλ: 235 nm; Flow Rate: 10 ml/min.

Solvent A is 100% 0.1% TFA/$H_2O$; Solvent B is 100% 0.08% TFA/ACN. The gradient is as follows.

| T (min) | % B (linear gradient) |
| --- | --- |
| 0 | 10 |
| 10 | 18 |
| 80 | 32 |
| 95 | 95 |

Fractions are analyzed by analytical HPLC and those that contain the desired peptide are combined. The acetonitrile is stripped and the resulting aqueous solution lyophilized. The resulting amide, containing sulfide bonds, is confirmed by mass spectrum.

5.2.3.2 Recombinant Synthesis

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Recombinantly produced forms of the protegrins may require subsequent derivatization to modify the N- and/or C-terminus and, depending on the isolation procedure, to effect the formation of disulfide bonds as described hereinabove. Depending on the host organism used for recombinant production and the animal source from which the protein is isolated, some or all of these conversions may already have been effected.

For recombinant production, the DNA encoding the protegrins of the invention is included in an expression system which places these coding sequences under control of a suitable promoter and other control sequences compatible with an intended host cell. Types of host cells available span almost the entire range of the plant and animal kingdoms. Thus, the protegrins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The protegrins of the invention can be produced in a form that will result in their secretion from the host cell by fusing to the DNA encoding the protegrin, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the protegrins of the invention can be produced in a variety of modalities including chemical synthesis and recombinant production or some combination of these techniques.

Any members of the protegrin class which occur naturally are supplied in purified and/or isolated form. By "purified and/or isolated" is meant free from the environment in which the peptide normally occurs (in the case of such naturally occurring peptides) and in a form where it can be used practically. Thus, "purified and/or isolated" form means that the peptide is substantially pure, i.e., more than 90% pure, preferably more than 95% pure and more preferably more than 99% pure or is in a completely different context such as that of a pharmaceutical preparation.

5.2.4 Compositions Containing the Protegrins and Methods of Use

The protegrins of the invention exhibit broad spectrum antimicrobial activity against a wide range of microbial and viral targets, including Gram-positive and Gram-negative bacteria, yeast, protozoa and certain strains of virus. Because of their broad spectrum of activities, the protegrins of the invention can be used as preservatives as well as in treatment and prophylactic contexts.

Gram-positive bacteria which the protegrins of the invention are bacteriocidal against include such major pathogens as *Staphylococcus aureus*, including MRSA (the methicillin resistant version) and MSSA (the methicillin-sensitive strain), and *Enterococcus faecium* and *E. faecalis* (including VREF or vancomycin resistant *E. faecium*) and VSEF or vancomycin-sensitive *E. faecalis*). These are very common pathogens in hospital settings. Other Gram-positive bacteria which are suitable targets include *Listeria monocytogenes, Streptococcus pneumoniae* (including PRSP, the penicillin resistant form), *S. mitis, S. sanguis, Staphylococcus epidermis* (including methicillin sensitive strain MSSE), *S. salivarius, Corynebacterium minutissium, C. pseudodiphtheriae, C. striatum,* Corynebacterium groups G1 and G2, and Bacillus subtilis. PRSP is also a wide-spread health hazard.

Among Gram-negative organisms against which the protegrins are effective are *Escherichia coli, Pseudomonas aeruginosa, Klebsiella pneumoniae, Serratia marcescens, Haemophilus influenzae, Salmonella typhimurium, Acinetobacter calocoaceticus, C. pneumoniae,* and *Neisseria meningitidus,* as well as other species including those within the genera represented above. For example, *Neisseria gonorrhoeae* is associated with sexually transmitted diseases (STDs) as is *Chlamydia trachomatis.* Also among the Gram-negative organisms are the gastric pathogens *Helicobacter pylori, H. felis,* and *Campylobacter jejuni.*

Besides Gram-positive and Gram-negative bacteria, the protegrins of the invention are also effective against growth and infection by mycobacteria such as *M. tuberculosis* and *M. avium* (including MAC); fungi, such as *Candida albicans* and the related pathogens, *C. parapsilosis, C. krusei, C. tropicalis* and *C. glabrata,* as well as *Aspergillus niger.* Among the viruses against which the protegrins are effective are *Herpes simplex* I and II and Human immunodeficiency virus (HIV).

The foregoing is not an exhaustive list, but representative of the microbes against which the protegrins of the invention are active.

As stated above, the protegrins can also be used in disinfectant compositions and as preservatives for materials such as foodstuffs, cosmetics, medicaments, or other materials containing nutrients for organisms. For use in such contexts, the protegrins are supplied either as a single protegrin, in admixture with several other protegrins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the protegrins of the invention can be formulated as pharmaceutical or veterinary compositions. Depending on the subject to be treated, the mode of administration, and the type of treatment desired—e.g., prevention, prophylaxis, therapy; the protegrins are formulated in ways consonant with these parameters. A summary of such techniques is found in Remington's *Pharmaceutical Sciences*, latest edition, Mack Publishing Co., Easton, Pa.

The protegrins can be used in animal subjects, including humans, both as therapeutic and prophylactic treatments; by "treating" an infection is meant either preventing it from occurring, ameliorating the symptoms, inhibiting the growth of the microbe in the subject, and any other negative effect on the microbe which is beneficial to the subject. Thus, "treating" or "treatment" have both prophylactic and therapeutic aspects.

The protegrins are particularly attractive as an active ingredient in pharmaceutical compositions useful in treatment of sexually transmitted diseases, including those caused by *Chlamydia trachomatis, Treponema pallidum, Neisseria gonorrhoeae, Trichomonas vaginalis, Herpes simplex* type 2 and HIV. Topical formulations are preferred and include creams, salves, oils, powders, gels and the like. Suitable topical excipients are well known in the art and can be adapted for particular uses by those of ordinary skill.

In general, for use in therapy or prophylaxis of STDs, the protegrins of the invention may be used alone or in combination with other antibiotics such as erythromycin, tetracycline, macrolides, for example azithromycin and the cephalosporins. Depending on the mode of administration, the protegrins will be formulated into suitable compositions to permit facile delivery to the affected areas. The protegrins may be used in forms containing one or two disulfide bridges or may be in linear form. In addition, use of the enantiomeric forms containing all D-amino acids may confer advantages such as resistance to those proteases, such as trypsin and chymotrypsin, to which the protegrins containing L-amino acids are less resistant.

The protegrins of the invention can be administered singly or as mixtures of several protegrins or in combination with other pharmaceutically active components. The formulations may be prepared in a manner suitable for systemic administration or topical or local administration. Systemic formulations include those designed for injection (e.g., intramuscular, intravenous, intraperitoneal or subcutaneous injection) or may be prepared for transdermal, transmucosal, or oral administration. The formulation will generally include a diluent as well as, in some cases, adjuvants, buffers, preservatives and the like. The protegrins can be administered also in liposomal compositions or as microemulsions.

If administration is to be oral, the protegrins of the invention should be protected from degradation in the digestive tract using a suitable enteric coating. This may be avoided to some extent by utilizing amino acids in the D-configuration, thus providing resistance to protease. The protegrins are relatively acid stable, however, some degree of enteric coating may still be required.

The protegrins of the invention retain their activity against microbes in the context of borate solutions that are commonly used in eye care products. It has also been shown that when tested for antimicrobial activity against *E. coli* in the presence and absence of lysozyme in borate buffered saline, that the presence of lysozyme enhanced the effectiveness of PG-3. This effect was more pronounced when the PG-3 was autoclaved and similar patterns were obtained for both the free-acid and the amide forms. Accordingly, the protegrins may be used as preservatives in such compositions or as antimicrobials for treatment of eye infections, such as conjunctivitis and corneal ulcers.

The protegrins retain their activity and have improved serum compatibility and/or reduced hemolytic activity against human red blood cells as compared with naturally-occurring protegrin PG-1 (SEQ ID NO:1). In addition, the protegrins of the invention are dramatically less cytotoxic with respect to the cells of higher organisms as compared with their toxicity to microbes. These properties make the protegrins of the invention particularly suitable for in vivo and therapeutic use, especially when administered intravenously.

The protegrins of the invention may also be applied to plants or to their environment to prevent virus- and microbe-induced diseases in these plants. Suitable compositions for this use will typically contain a diluent as well as a spreading agent or other ancillary agreements beneficial to the plant or to the environment.

Thus, the protegrins of the invention may be used in any context wherein an antimicrobial and/or antiviral action is required. This use may be an entirely in vitro use, or the peptides may be administered to organisms, including humans.

In addition, the antimicrobial or antiviral activity may be generated in situ by administering an expression system suitable for the production of the protegrins of the invention. Such expression systems can be supplied to plant and animal subjects, including humans, using known techniques. For example, in animals, pox-based expression vectors can be used to generate the peptides in situ. Similarly, plant cells can be transformed with expression vectors and then regenerated into whole plants which are capable of their own production of the peptides.

The protegrins are also capable of inactivating endotoxins derived from Gram-negative bacteria—i.e., lipopolysaccharides (LPS)—in standard assays. Accordingly, the protegrins may be used under any circumstances where inactivation of LPS is desired. One such situation is in the treatment or amelioration of Gram-negative sepsis.

5.3 Effective Dosages

The peptides of the invention, or compositions thereof, will generally be used in an amount effective to achieve the intended purpose. Of course, it is to be understood that the amount used will depend on the particular application.

For example, for use as a disinfectant or preservative, an antimicrobially effective amount of a peptide, or composition thereof, is applied or added to the material to be disinfected or preserved. By antimicrobially effective amount is meant an amount of peptide or composition that inhibits the growth of, or is lethal to, a target microbe population. While the actual antimicrobially effective amount will depend on a particular application, for use as a disinfectant or preservative the peptides, or compositions thereof, are usually added or applied to the material to be disinfected or preserved in relatively low amounts. Typically, the peptide comprises less than about 5% by weight of the disinfectant solution or material to be preserved, preferably less than about 1% by weight and more preferably less than about 0.1% by weight. An ordinarily skilled artisan will be able to determine antimicrobially effective amounts of particular peptides for particular applications without undue experimentation using, for example, the in vitro assays provided in the examples.

For use to treat or prevent microbial infections or diseases related thereto, the peptides of the invention, or compositions thereof, are administered or applied in a therapeutically effective amount. By therapeutically effective amount is meant an amount effective top ameliorate the symptoms of, or ameliorate, treat or prevent microbial infections or diseases related thereto. Determination of a therapeutically effective amount is well within the capabilities of those skilled in the art, especially in light of the detailed disclosure provided herein.

As in the case of disinfectants and preservatives, for topical administration to treat or prevent bacterial, yeast, fungal or other infections a therapeutically effective dose can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating peptide concentration range that includes the $IC_{50}$ as determined in cell culture (i.e., the concentration of test compound that is lethal to 50% of a cell culture), the MIC, as determined in cell culture (i.e., the minimal inhibitory concentration for growth) or the $IC_{100}$ as determined in cell culture (i.e., the concentration of peptide that is lethal to 100% of a cell culture). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the active peptide which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of peptide may not be related to plasma concentration. One having skill in the art will be able to optimize therapeutically effective local dosages without undue experimentation.

The amount of peptide administered will, of course, be dependent on the subject being treated, on the subject's weight, the severity of the affliction, the manner of administration and the judgment of the prescribing physician.

The antimicrobial therapy may be repeated intermittently while infections are detectable or even when they are not detectable. The therapy may be provided alone or in combination with other drugs, such as for example antibiotics or other antimicrobial peptides.

5.4 Toxicity

Preferably, a therapeutically effective dose of the peptides described herein will provide therapeutic benefit without causing substantial toxicity. Toxicity of the peptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the peptides described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

The invention having been described, the following Examples are intended to illustrate, not limit, the invention.

6. EXAMPLE: SERUM AVAILABILITY

Exemplary peptides [$^5$T]PG-1 (SEQ ID NO:3), OGGOTCYCOOOFCVCVGO-NH$_2$ (SEQ ID NO:4), OTTLCYCOGOFCVCVGO-NH$_2$ (SEQ ID NO:10), OTOLCYCOZOFCVCV-NH$_2$ (Z-MeGly; SEQ ID NO:11) and WTCYCOOOFCVCV-NH$_2$ (SEQ ID NO:14) were tested in vitro for serum availability according to the MCZ assay described in WO 97/18826. Peptide was tested at 50 µg/ml against two different strains of indicator bacteria (*E. coli* and VRE) both in the presence and absence of serum. For experiments performed in the presence of serum, 90% serum was used as the peptide diluent. Native PG-1 (SEQ ID NO:1) was tested as a control.

6.1 Results

The results of the availability assay are provided in TABLE 3, below. Percent availability refers to the activity of the indicated peptide in serum as compared with the activity of the same peptide in the absence of serum (assigned a value of 100%).

TABLE 3

| In Vitro Serum Availability (%) at 50 µg/mL Peptide | | |
|---|---|---|
| Peptide | AVAILABILITY (%) | |
| | *E. coli* | VRE |
| Native PG-1 (SEQ ID NO:1) | 3 | 1.6 |
| [$^5$T]PG-1 (SEQ ID NO:3) | 10 | 1.6 |
| OGGQTCYCOOOFCVCVGO-NH$_2$ (SEQ ID NO:4) | 40 | 9 |
| OTOLCYCOZOFCVCV-NH$_2$ (Z = MeGLY) (SEG ID NO: 11) | 30 | 8 |
| OTTLCYCOGOFCVCVGO-NH$_2$ (SEQ ID NO:10) | 10 | 3 |
| WTCYCOOOFCVCV (SEQ ID NO:14) | 4 | 2 |

As can be seen from TABLE 3, threonine-containing analogues had significantly higher serum availability than native protegrin PG-1.

Analogues containing threonines and non-arginine basic amino acids exhibited the most dramatic increase in serum availability.

7. EXAMPLE: ANTIMICROBIAL ACTIVITY

The antimicrobial activity of several exemplary peptides of the invention was demonstrated against a variety of microbes, including *E. coli* ML-35, *L. monocytegenes*, *Pseudomonas aruginosa* (Psa), methicillin resistant *Staphylococcus aureus* (MRSA), vancomycin resistant *Enterococcus faecium* (VREF) and *Candida albicans* (C. alb). Methods were as described in WO 97/18826.

7.1 Results

The results of the assay are presented in FIGS. 2–5 and TABLE 4, below.

TABLE 4

MIC Values (μg/ml) of Exemplary Peptides

| Peptide Sequence | | Psa | MRSA | VREF | C. alb. |
|---|---|---|---|---|---|
| RGGRLCYCRRRFCVCVGR-NH$_2$ | (SEQ ID NO:1) | 1 | 8 | 0.5 | 8 |
| RGGRTCYCRRRFCVCVGR-NH$_2$ | (SEQ ID No:3) | 2 | 8 | 0.3 | 8 |
| OGGOTCYCOOOFCVCVGO-NH$_2$ | (SEQ ID NO:4) | 1 | >64 | 3.3 | >64 |
| OTT LCYCOGOFCVCVGO-NH$_2$ | (SEQ ID NO:10) | 0.5 | 32 | 1 | 32 |
| OTOLCYCOZOFCVCV-NH$_2$ | (SEQ ID NO:11) | 2 | 64 | 8 | >64 |
| *XTXLCYCXXXFCTCV-NH$_2$ | (SEQ ID NO:12) | 1.3 | 16 | 1 | 8 |
| WTCYCOOOFCVCV-NH$_2$ | (SEQ ID NO:14) | 1 | 16 | 0.25 | 1.6 |
| JTCYCOOOFCVCV-NH$_2$ | (SEQ ID NO:15) | 2 | 32 | 6.67 | >64 |
| JLCFCOOOFCTCV-NH$_2$ | (SEQ ID NO:16) | 4 | 64 | 2 | 64 |
| JTCFCOOOFCTCV-NH$_2$ | (SEQ ID NO:17) | 16 | >128 | 32 | >128 |

J is N-ε-tryptophanyl-lysine, X is Dbu, Z is MeGly and * indicates peptides acylated at the N-terminus with (C$_8$H$_{18}$—C(O)—).

As can be seen in FIGS. 2–6 and TABLE 4, exemplary protegrin peptides of the invention exhibit antimicrobial activity against a wide variety of pathogens that is equivalent to, or even exceeds, that of native protegrin PG-1 (SEQ ID NO:1).

8. EXAMPLE: HEMOLYTIC ACTIVITY

Native protegrin PG-1 (SEQ ID NO:1) and exemplary peptides [$^5$T]PG-1 (SEQ ID NO:3), [$^7$T]PG-1 (SEQ ID NO:5), [$^{14}$T]PG-1 (SEQ ID NO:6) and [$^{16}$T]PG-1 (SEQ ID NO:8) were tested for hemolytic activity against human red blood cells. Melittin (GIGAVLKVLTTGLPALISWIKRKRQQ-NH$_2$; SEQ ID NO:19) was tested as a positive control. In the assay, various concentrations of peptides were incubated with human red blood cells and the percentage of hemolysis determined.

8.1 Results

The results of the hemolysis assay are presented in FIG. 1. The threonine-containing protegrins were substantially less hemolytic against human cells than either melittin (positive control) or native protegrin PG-1. At concentrations exceeding 5 μg/ml, all of the threonine variants tested were less hemolytic than either melittin or native protegrin PG-1. The decrease in hemolysis for the threonine variants is even more pronounced at concentrations exceeding 10 μg/ml.

9. EXAMPLE: CYTOTOXICITY

The cytotoxicity of exemplary protegrins [5T]PG-1 (SEQ ID NO:3), [$^7$T]PG-1 (SEQ ID NO:5), [$^{14}$T] (SEQ ID NO:6) and [$^{16}$T]PG-1 (SEQ ID NO:8) was tested against ME-180 (human cervical carcinoma) cells using an MTT assay.

Native protegrin PG-1 (SEQ ID NO:1) and melittin (SEQ ID NO:19) were tested as controls.

9.1 Results

The results of the MTT assay are provided in FIG. 6 and TABLE 5, below.

TABLE 5

RESULTS OF MTT ASSAY

| PEPTIDE | | EC$_{50}$ (μg/mL) |
|---|---|---|
| Melittin | (SEQ ID NO: 19) | 8.0 |
| Native PG-1 | (SEQ ID NO: 1) | 47.2 |
| [$^5$T] PG-1 | (SEQ ID NO: 3) | 101.3 |
| [$^7$T] PG-1 | (SEQ ID NO: 5) | 50.4 |
| [$^{14}$T] PG-1 | (SEQ ID NO: 6) | 154.8 |
| [$^{16}$T] PG-1 | (SEQ ID NO: 8) | 122.6 |

The results show that threonine-containing protegrins such as [$^{14}$T]PG-1 are less cytotoxic than native PG-1 and the control peptide melittin. These peptides do, however, maintain or improve their antimicrobial activity over native PG-1 (FIGS. 2–5 and TABLE 4).

The present invention is not to be limited in scope by the exemplified embodiments, which are intended as illustrations of single aspects of the invention, and any sequences which are functionally equivalent are within the scope of the invention. Indeed, various modifications of the invention in addition to those described above will become apparent to those skilled in the art from the foregoing description and accompanying drawings. Such modifications are intended to fall within the scope of the appended claims.

All references cited herein are hereby incorporated herein in their entireties by reference.

What is claimed is:

1. An antimicrobial peptide composed of 10–30 amino acid residues comprising the amino acid sequence:

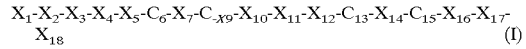

$$X_1\text{-}X_2\text{-}X_3\text{-}X_4\text{-}X_5\text{-}C_6\text{-}X_7\text{-}C_{x9}\text{-}X_{10}\text{-}X_{11}\text{-}X_{12}\text{-}C_{13}\text{-}X_{14}\text{-}C_{15}\text{-}X_{16}\text{-}X_{17}\text{-}X_{18} \quad (I)$$

or a pharmaceutically acceptable salt or an N-terminal acylated or a C-terminal amidated or esterified form thereof, wherein:
- each of $C_8$ and $C_{13}$ is independently present or not present, and if present each is independently a cysteine-like, basic, small, polar or hydrophobic amino acid;
- each of $C_6$ and $C_{15}$ is independently a cysteine-like, basic, small, polar or hydrophobic amino acid;
- each of $X_1$, $X_2$, $X_3$, $X_4$ and $X_5$ is independently present or not present, and if present each is independently a basic, hydrophobic, polar or small amino acid;
- each of $X_7$ and $X_{14}$ is independently a hydrophobic or a small amino acid;
- each of $X_9$ and $X_{12}$ is independently present or not present;
- $X_9$–$X_{12}$ taken together are capable of effecting a reverse turn when contained in the amino acid sequence of formula (I) and at least one of $X_9$–$X_{12}$ must be a basic amino acid;
- each of $X_{16}$, $X_{17}$ and $X_{18}$ is independently present or not present, and if present each is independently a basic, hydrophobic, polar or small amino acid; and
- at least about 15% up to about 50% of the amino acids comprising said antimicrobial peptide are basic amino acids such that said antimicrobial peptide has a net charge of at least +1 at physiological pH;
- with the proviso that at least one of $X_5$, $X_7$, or $X_{14}$ is a small, hydroxyl-containing amino acid.

2. The antimicrobial peptide of claim 1, in which $C_6$, $C_8$, $C_{13}$ and $C_{15}$ are each Cys and which is in the native form.

3. The antimicrobial peptide of claim 1 which is C-terminal amidated.

4. The antimicrobial peptide of claim 1 in which at least one of $X_5$, $X_7$, or $X_{14}$ is T.

5. The antimicrobial peptide of claim 1, which is composed of 10–18 amino acid residues.

6. The antimicrobial peptide of claim 1 in which at least one basic amino acid is other than R.

7. The antimicrobial peptide of claim 1 in which all basic amino acids are each independently selected from the group consisting of Orn, K and Dab.

8. The antimicrobial peptide of claim 1 in which $X_9$–$X_{12}$, taken together are a three amino acid residue γ-turn.

9. The antimicrobial peptide of claim 1 in which $X_9$–$X_{12}$ taken together are a four amino acid residue β-turn.

10. The antimicrobial peptide of claim 1, wherein said β-turn is selected from the group consisting of ZZZG; ZZZF; ZZZY; ZZSG; ZZAL; ZGZL; ZXZF; ZFZL; ZPZV; ZPZF; ZGZY; ZGZF; IZGZ; LZZF; YZZY; ZZZE; YZZV; and YZGZ, wherein X is MeGly and each Z is independently an L- or D-enantiomer of R, K, Dab, Dbu or Orn.

11. A pharmaceutical composition comprising an antimicrobial peptide according to claim 1 and at least one pharmaceutically acceptable carrier, diluent or excipient.

12. An environmental composition for application to plants or plant environments comprising an antimicrobial peptide according to claim 1 and at least one environmentally acceptable carrier, diluent or excipient.

13. A method to inhibit the growth of a microbe comprising the step of contacting said microbe with an effective amount of an antimicrobial peptide according to claim 1.

14. A method to inactivate the endotoxin of Gram-negative bacteria comprising the step of contacting said endotoxin with an effective amount an antimicrobial peptide according to claim 1.

15. A method to treat or prevent a microbial infection or a disease related thereto, said method comprising the step of administering to a subject in need of such treatment a therapeutically effective amount of an antimicrobial peptide according to claim 1.

16. The method of claim 15 wherein the microbial infection is caused by *Staphylococcus aureus*.

17. The method of claim 15, wherein the microbial infection is caused by Pseudomonas.

18. The method of claim 15, wherein the microbial infection is caused by *H. pylori*.

19. The method of claim 15, wherein said infection is caused by an antibiotic-resistant bacterium.

20. An antimicrobial peptide comprising an amino acid sequence selected from the group consisting of:

| | | |
|---|---|---|
| [³T]PG-1: | RGTRLCYCRRRFCVCVGR | (SEQ ID NO:2); |
| [⁵T]PG-1: | RGGRTCYCRRRFCVCVGR | (SEQ ID NO:3); |
| | OGGOTCYCOOOFCVCVGO | (SEQ ID NO:4); |
| [⁷T]PG-1: | RGGRLCTCRRRFCVCVGR | (SEQ ID NO:5); |
| [¹⁴T]PG-1: | RGGRLCYCRRRFCTCVGR | (SEQ ID NO:6); |
| | OGGOLCYCOOOFCTCVGO | (SEQ ID NO:7); |
| [¹⁶T]PG-1: | RGGRLCYCRRRFCVCTGR | (SEQ ID NO:8); |
| | OGGOLCYCOOOFCVCTGO | (SEQ ID NO:9); |
| | OTT LCYCOGOFCVCVGO | (SEQ ID NO:10); |
| | OTOLCYCOZOPCVCV | (SEQ ID NO:11); |
| | XTXLCYCXXXFCTCV | (SEQ ID NO:12); |
| | XTXOCYCXXXYCTCV | (SEQ ID NO:13); |
| | WTCYCOOOFCVCV | (SEQ ID NO:14); |
| | JTCYCOOOFCVCV | (SEQ ID NO:15); |
| | JLCFCOOOFCTCV | (SEQ ID NO:16); |
| | JTCFCOOOFCTCV | (SEQ ID NO:17); and |
| | HTHLCYXXVCV | (SEQ ID NO:18) | or a pharmaceutically acceptable salt or an N-terminal acylated or a C-terminal amidated or esterified form thereof, wherein J is N-ε-tryptophanyl-Lysine, X is Dbu and Z is MeGly.

21. A pharmaceutical composition comprising an antimicrobial peptide according to claim 20 and at least one pharmaceutically acceptable carrier, diluent or excipient.

22. An environmental composition for application to plants or plant environments comprising an antimicrobial peptide according to claim 20 and at least one environmentally acceptable carrier, diluent or excipient.

23. A method to inhibit the growth of a microbe comprising the step of contacting said microbe with an effective amount of an antimicrobial peptide according to claim 20.

24. A method to inactivate the endotoxin of Gram-negative bacteria comprising the step of contacting said endotoxin with an effective amount an antimicrobial peptide according to claim 20.

25. A method to treat or prevent a microbial infection or a disease related thereto, said method comprising the step of administering to a subject in need of such treatment a therapeutically effective amount of an antimicrobial peptide according to claim 20.

26. The method of claim 25 wherein the microbial infection is caused by *Staphylococcus aureus*.

27. The method of claim 25, wherein the microbial infection is caused by Pseudomonas.

28. The method of claim 25, wherein the microbial infection is caused by *Helicobacter pylori*.

29. The method of claim 25, wherein said infection is caused by an antibiotic-resistant bacterium.

* * * * *

UNITED STATES PATENT AND TRADEMARK OFFICE
CERTIFICATE OF CORRECTION

PATENT NO. : 6,043,220  
DATED : March 28, 2000  
INVENTOR(S) : Chang et al.

Page 1 of 1

It is certified that error appears in the above-identified patent and that said Letters Patent is hereby corrected as shown below:

Column 41,  
Lines 35-36, delete "$X_1$-$X_2$-$X_3$-$X_4$-$X_5$-$C_6$-$X_7$-$C_{-X9}$-$X_{10}$-$X_{11}$-$X_{12}$-$C_{13}$-$X_{14}$-$C_{15}$-$X_{16}$-$X_{17}$-$X_{18}$" and replace with -- $X_1$-$X_2$-$X_3$-$X_4$-$X_5$-$C_6$-$X_7$-$C_8$-$X_9$-$X_{10}$-$X_{11}$-$X_{12}$-$C_{13}$-$X_{14}$-$C_{15}$-$X_{16}$-$X_{17}$-$X_{18}$ --

Column 42,  
Line 46, delete "claim 1" and repalce with -- claim 9 --

Signed and Sealed this

Twenty-fifth Day of June, 2002

*Attest:*

JAMES E. ROGAN  
*Attesting Officer*     *Director of the United States Patent and Trademark Office*

UNITED STATES PATENT AND TRADEMARK OFFICE
CERTIFICATE OF CORRECTION

PATENT NO. : 6,043,220 Page 1 of 1
APPLICATION NO. : 08/984294
DATED : March 28, 2000
INVENTOR(S) : Conway C. Chang et al.

It is certified that error appears in the above-identified patent and that said Letters Patent is hereby corrected as shown below:

Col. 1, under the title, please insert:

--Statement of Rights to Inventions Made Under Federally Sponsored Research

This invention was made with Government support of Grant No. AI022839 and AI037945 awarded by the National Institutes of Health. The Government has certain rights in this invention.--

Signed and Sealed this

Fifth Day of May, 2009

JOHN DOLL
*Acting Director of the United States Patent and Trademark Office*

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 18 amino acids
      (B) TYPE: amino acid (C) STRANDEDNESS: single
            (D) TOPOLOGY: linear (ii) MOLECULE TYPE: None (xi) SEQUENCE DESCRIPTION: SEQ ID NO:1:

Arg Gly Gly Arg Leu Cys Tyr Cys Arg Arg Arg Phe Cys Val Cys Val
 1               5                  10                  15

Gly Arg (2) INFORMATION FOR SEQ ID NO:2:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:2:

Arg Gly Thr Arg Leu Cys Tyr Cys Arg Arg Arg Phe Cys Val Cys Val
 1               5                  10                  15

Gly Arg (2) INFORMATION FOR SEQ ID NO:3:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:3:

Arg Gly Gly Arg Thr Cys Tyr Cys Arg Arg Arg Phe Cys Val Cys Val
 1               5                  10                  15

Gly Arg (2) INFORMATION FOR SEQ ID NO:4:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = Orn
            (A) NAME/KEY: Other
            (B) LOCATION: 4
            (D) OTHER INFORMATION: Xaa = Orn
            (A) NAME/KEY: Other
            (B) LOCATION: 9
            (D) OTHER INFORMATION: Xaa = Orn
            (A) NAME/KEY: Other
            (B) LOCATION: 10
            (D) OTHER INFORMATION: Xaa = Orn
            (A) NAME/KEY: Other
            (B) LOCATION: 11
            (D) OTHER INFORMATION: Xaa = Orn
            (A) NAME/KEY: Other
            (B) LOCATION: 18
            (D) OTHER INFORMATION: Xaa = Orn (xi) SEQUENCE DESCRIPTION: SEQ ID NO:4:

Xaa Gly Gly Xaa Thr Cys Tyr Cys Xaa Xaa Xaa Phe Cys Val Cys Val
 1               5                  10                  15

Gly Xaa (2) INFORMATION FOR SEQ ID NO:5:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:5:

Arg Gly Gly Arg Leu Cys Thr Cys Arg Arg Arg Phe Cys Val Cys Val
 1               5                  10                  15

Gly Arg (2) INFORMATION FOR SEQ ID NO:6:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:6:

Arg Gly Gly Arg Leu Cys Tyr Cys Arg Arg Arg Phe Cys Thr Cys Val
 1               5                  10                  15

Gly Arg (2) INFORMATION FOR SEQ ID NO:7:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = Orn
            (A) NAME/KEY: Other
            (B) LOCATION: 4
            (D) OTHER INFORMATION: Xaa = Orn
            (A) NAME/KEY: Other
            (B) LOCATION: 9
            (D) OTHER INFORMATION: Xaa = Orn
            (A) NAME/KEY: Other
            (B) LOCATION: 10
            (D) OTHER INFORMATION: Xaa = Orn
            (A) NAME/KEY: Other
            (B) LOCATION: 11
            (D) OTHER INFORMATION: Xaa = Orn
            (A) NAME/KEY: Other
            (B) LOCATION: 18
            (D) OTHER INFORMATION: Xaa = Orn (xi) SEQUENCE DESCRIPTION: SEQ ID NO:7:

Xaa Gly Gly Xaa Leu Cys Tyr Cys Xaa Xaa Xaa Phe Cys Thr Cys Val
 1               5                  10                  15

```
Gly Xaa (2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

Arg Gly Gly Arg Leu Cys Tyr Cys Arg Arg Arg Phe Cys Val Cys Thr
1               5                   10                  15

Gly Arg (2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = Orn
        (A) NAME/KEY: Other
        (B) LOCATION: 4
        (D) OTHER INFORMATION: Xaa = Orn
        (A) NAME/KEY: Other
        (B) LOCATION: 9
        (D) OTHER INFORMATION: Xaa = Orn
        (A) NAME/KEY: Other
        (B) LOCATION: 10
        (D) OTHER INFORMATION: Xaa = Orn
        (A) NAME/KEY: Other
        (B) LOCATION: 11
        (D) OTHER INFORMATION: Xaa = Orn
        (A) NAME/KEY: Other
        (B) LOCATION: 18
        (D) OTHER INFORMATION: Xaa = Orn (xi) SEQUENCE DESCRIPTION: SEQ ID NO:9:

Xaa Gly Gly Xaa Leu Cys Tyr Cys Xaa Xaa Xaa Phe Cys Val Cys Thr
1               5                   10                  15

Gly Xaa (2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = Orn
        (A) NAME/KEY: Other
        (B) LOCATION: 8
        (D) OTHER INFORMATION: Xaa = Orn
        (A) NAME/KEY: Other
        (B) LOCATION: 10
        (D) OTHER INFORMATION: Xaa = Orn
```

-continued (A) NAME/KEY: Other
            (B) LOCATION: 17
            (D) OTHER INFORMATION: Xaa = Orn (xi) SEQUENCE DESCRIPTION: SEQ ID NO:10:

Xaa Thr Thr Leu Cys Tyr Cys Xaa Gly Xaa Phe Cys Val Cys Val Gly
 1               5                  10                  15

Xaa (2) INFORMATION FOR SEQ ID NO:11:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = Orn
            (A) NAME/KEY: Other
            (B) LOCATION: 3
            (D) OTHER INFORMATION: Xaa = Orn
            (A) NAME/KEY: Other
            (B) LOCATION: 8
            (D) OTHER INFORMATION: Xaa = Orn
            (A) NAME/KEY: Other
            (B) LOCATION: 9
            (D) OTHER INFORMATION: Xaa = MeGly
            (A) NAME/KEY: Other
            (B) LOCATION: 10
            (D) OTHER INFORMATION: Xaa = Orn (xi) SEQUENCE DESCRIPTION: SEQ ID NO:11:

Xaa Thr Xaa Leu Cys Tyr Cys Xaa Xaa Xaa Phe Cys Val Cys Val
 1               5                  10                  15

(2) INFORMATION FOR SEQ ID NO:12:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = Dbu
            (A) NAME/KEY: Other
            (B) LOCATION: 3
            (D) OTHER INFORMATION: Xaa = Dbu
            (A) NAME/KEY: Other
            (B) LOCATION: 8
            (D) OTHER INFORMATION: Xaa = Dbu
            (A) NAME/KEY: Other
            (B) LOCATION: 9
            (D) OTHER INFORMATION: Xaa = Dbu
            (A) NAME/KEY: Other
            (B) LOCATION: 10
            (D) OTHER INFORMATION: Xaa = Dbu (xi) SEQUENCE DESCRIPTION: SEQ ID NO:12:

Xaa Thr Xaa Leu Cys Tyr Cys Xaa Xaa Xaa Phe Cys Thr Cys Val
 1               5                  10                  15

(2) INFORMATION FOR SEQ ID NO:13:

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = Dbu
        (A) NAME/KEY: Other
        (B) LOCATION: 3
        (D) OTHER INFORMATION: Xaa = Dbu
        (A) NAME/KEY: Other
        (B) LOCATION: 8
        (D) OTHER INFORMATION: Xaa = Dbu
        (A) NAME/KEY: Other
        (B) LOCATION: 9
        (D) OTHER INFORMATION: Xaa = Dbu
        (A) NAME/KEY: Other
        (B) LOCATION: 10
        (D) OTHER INFORMATION: Xaa = Dbu (xi) SEQUENCE DESCRIPTION: SEQ ID NO:13:

Xaa Thr Xaa Gln Cys Tyr Cys Xaa Xaa Xaa Tyr Cys Thr Cys Val
 1               5                  10                  15

(2) INFORMATION FOR SEQ ID NO:14:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 6
        (D) OTHER INFORMATION: Xaa = Orn
        (A) NAME/KEY: Other
        (B) LOCATION: 7
        (D) OTHER INFORMATION: Xaa = Orn
        (A) NAME/KEY: Other
        (B) LOCATION: 8
        (D) OTHER INFORMATION: Xaa = Orn (xi) SEQUENCE DESCRIPTION: SEQ ID NO:14:

Trp Thr Cys Tyr Cys Xaa Xaa Xaa Phe Cys Val Cys Val
 1               5                  10

(2) INFORMATION FOR SEQ ID NO:15:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = N-n-tryptophanyl-Lysine
        (A) NAME/KEY: Other
        (B) LOCATION: 6
        (D) OTHER INFORMATION: Xaa = Orn
        (A) NAME/KEY: Other
        (B) LOCATION: 7
        (D) OTHER INFORMATION: Xaa = Orn
```

(A) NAME/KEY: Other
            (B) LOCATION: 8
            (D) OTHER INFORMATION: Xaa = Orn (xi) SEQUENCE DESCRIPTION: SEQ ID NO:15:

Xaa Thr Cys Tyr Cys Xaa Xaa Xaa Phe Cys Val Cys Val
 1               5                   10

(2) INFORMATION FOR SEQ ID NO:16:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = N-n-tryptophanyl-Lysine
            (A) NAME/KEY: Other
            (B) LOCATION: 6
            (D) OTHER INFORMATION: Xaa = Orn
            (A) NAME/KEY: Other
            (B) LOCATION: 7
            (D) OTHER INFORMATION: Xaa = Orn
            (A) NAME/KEY: Other
            (B) LOCATION: 8
            (D) OTHER INFORMATION: Xaa = Orn (xi) SEQUENCE DESCRIPTION: SEQ ID NO:16:

Xaa Leu Cys Phe Cys Xaa Xaa Xaa Phe Cys Thr Cys Val
 1               5                   10

(2) INFORMATION FOR SEQ ID NO:17:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1
            (D) OTHER INFORMATION: Xaa = N-n-tryptophanyl-Lysine
            (A) NAME/KEY: Other
            (B) LOCATION: 6
            (D) OTHER INFORMATION: Xaa = Orn
            (A) NAME/KEY: Other
            (B) LOCATION: 7
            (D) OTHER INFORMATION: Xaa = Orn
            (A) NAME/KEY: Other
            (B) LOCATION: 8
            (D) OTHER INFORMATION: Xaa = Orn (xi) SEQUENCE DESCRIPTION: SEQ ID NO:17:

Xaa Thr Cys Phe Cys Xaa Xaa Xaa Phe Cys Thr Cys Val
 1               5                   10

(2) INFORMATION FOR SEQ ID NO:18:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: None

```
    (ix) FEATURE:
         (A) NAME/KEY: Other
         (B) LOCATION: 7
         (D) OTHER INFORMATION: Xaa = Dbu
         (A) NAME/KEY: Other
         (B) LOCATION: 8
         (D) OTHER INFORMATION: Xaa = Dbu (xi) SEQUENCE DESCRIPTION: SEQ ID NO:18:

His Thr His Leu Cys Tyr Xaa Xaa Val Cys Val
1               5                   10

(2) INFORMATION FOR SEQ ID NO:19:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```